(12) United States Patent
Pierman et al.

(10) Patent No.: US 12,171,477 B1
(45) Date of Patent: Dec. 24, 2024

(54) SURGICAL SCREW CADDY

(71) Applicants: Peter Eric Pierman, Carlsbad, CA (US); Casey M. Chambers, Carlsbad, CA (US)

(72) Inventors: Peter Eric Pierman, Carlsbad, CA (US); Casey M. Chambers, Carlsbad, CA (US)

( * ) Notice: Subject to any disclaimer, the term of this patent is extended or adjusted under 35 U.S.C. 154(b) by 0 days.

(21) Appl. No.: 18/438,429

(22) Filed: Feb. 10, 2024

(51) Int. Cl.
*A61B 17/86* (2006.01)
*A61B 17/00* (2006.01)

(52) U.S. Cl.
CPC .......... *A61B 17/865* (2013.01); *A61B 17/866* (2013.01); *A61B 2017/0046* (2013.01)

(58) Field of Classification Search
None
See application file for complete search history.

(56) References Cited

U.S. PATENT DOCUMENTS

| | | | |
|---|---|---|---|
| 5,445,641 A | 8/1995 | Frigg et al. |
| 5,925,048 A | 7/1999 | Ahmad et al. |
| 6,328,746 B1 | 12/2001 | Gambale |
| 7,461,574 B2 | 12/2008 | Lewis et al. |
| 7,572,264 B2 | 8/2009 | Null et al. |
| 7,588,576 B2 | 9/2009 | Teague et al. |
| 7,650,991 B2 | 1/2010 | Hester et al. |
| 7,722,623 B2 | 5/2010 | Franks et al. |
| 7,766,920 B2 | 8/2010 | Ciccone et al. |
| 7,771,429 B2 | 8/2010 | Ballard et al. |
| 7,846,167 B2 | 12/2010 | Garcia et al. |
| 8,016,836 B2 | 9/2011 | Corrao et al. |
| 8,087,325 B2 | 1/2012 | Neubardt |
| 8,382,810 B2 | 2/2013 | Peterson et al. |
| 8,540,756 B2 | 9/2013 | Olsen et al. |
| 9,271,732 B2 | 3/2016 | Walker |
| 9,284,110 B2 | 3/2016 | Garcia et al. |
| 9,572,611 B2 | 2/2017 | Wand |
| 9,918,755 B2 | 3/2018 | Bootwala et al. |
| 10,070,860 B2 | 9/2018 | Zergiebel |
| 10,226,290 B2 | 3/2019 | Steffensmeier et al. |
| 10,286,532 B2 | 5/2019 | Garcia et al. |
| 10,433,882 B2 | 10/2019 | O'Neil et al. |
| 10,531,903 B2 | 1/2020 | Daly et al. |
| 10,758,290 B2 | 9/2020 | Detweiler et al. |
| 10,820,911 B2 | 11/2020 | Delman et al. |
| 11,033,284 B2 | 6/2021 | Tsai et al. |
| 11,154,337 B2 | 10/2021 | Zollmann et al. |

(Continued)

FOREIGN PATENT DOCUMENTS

EP     1389964 B1    2/2004

*Primary Examiner* — Tessa M Matthews
(74) *Attorney, Agent, or Firm* — John M. Rogitz; John L. Rogitz

(57) ABSTRACT

A screw caddy device has material and structure to stabilize surgical screws for transport and engagement with a patient. The device includes non-rigid elastomeric material. The non-rigid elastomeric material is formed with openings to receive the screws for transport and to stabilize the screws while being extended into the patient. Lower exterior surfaces of the non-rigid elastomeric material may even be configured to engage holes in a surgical plate to assist with extending the screws into the plate and patient. Also disclosed are methods for manufacturing, providing, and using screw caddy device(s) consistent with present principles.

20 Claims, 44 Drawing Sheets

(56) References Cited

U.S. PATENT DOCUMENTS

| | | |
|---|---|---|
| 11,279,008 B2 | 3/2022 | Bethoux et al. |
| 11,337,743 B1 | 5/2022 | Nasr |
| 11,439,447 B2 | 9/2022 | Detweiler et al. |
| 2013/0060288 A1* | 3/2013 | Rodgers ............... A61B 17/808 606/283 |
| 2017/0135827 A1* | 5/2017 | O'Neil .................. A61F 2/4684 |
| 2019/0380755 A1* | 12/2019 | Tsai ................... A61B 17/8085 |
| 2020/0337751 A1* | 10/2020 | Detweiler ........... A61B 17/8038 |

* cited by examiner

SURGICAL SCREW CADDY

FIELD

The disclosure below relates generally to surgical screw caddies for use in craniomaxillofacial (CMF) fracture reductions and other surgical procedures.

BACKGROUND

Miniature surgical screws are often difficult to package, handle, deliver, and trace. Current surgical room techniques involve loading the screw onto a screwdriver tip (or blade tip) at a back table and then moving the screw and screwdriver together to the patient. The surgeon then attempts to insert the screw into a surgical plate hole using the screwdriver, which requires precision or else the screw can become dislodged from the driver and dropped. Even if aligned correctly with the plate hole, it is often difficult to then stably drive the screw through the plate hole and into the bone of the patient, creating more opportunity for dislodgement of the screw as well as less than optimal screw positioning within the patient themselves.

SUMMARY

Accordingly, the disclosure below relates to surgical screw caddies/loaders that can be used in sterile surgical environments. Each caddy may use material and structure to stabilize the screws while being transported from a surgical back table to the patient themselves, and to stabilize the screws while being driven through the caddy and into the patient.

Accordingly, in one aspect a medical device includes a cartridge. The cartridge includes a first opening configured to receive a screw. The first opening is formed at least in part by a non-rigid elastomeric material. The non-rigid elastomeric material is configured on the cartridge to stabilize the screw within the cartridge. The medical device also includes a rigid member engaged with an upper surface of the cartridge. The rigid member includes a second opening that aligns with the first opening for the screw to pass through the second opening and into the first opening for engagement with the non-rigid elastomeric material.

In various examples, the non-rigid elastomeric material itself may include silicone, thermoplastic elastomer, and/or other elastomer(s).

In some implementations, the cartridge and rigid member may establish at least part of a head that is engageable with a handle, and the medical device may even include the handle itself. The handle may be integral with at least a portion of the head, or may be detachable from the head. If detachable from the head, in specific examples the handle and head may be engageable with each other via a ball and socket assembly. Additionally, if desired the medical device may include the ball and socket assembly itself, with the ball of the ball and socket assembly being disposed on the head and with the socket of the ball and socket assembly being disposed on the handle. The medical device may even include a locking mechanism to lock the ball into the socket to secure the head on the handle while still allowing articulation of the head with respect to the handle.

If desired, the medical device may include and/or be vended with the screw(s) themselves.

Also in various example embodiments, an exterior surface of the non-rigid elastomeric material may taper distally at a distal end portion to receive a hole of a surgical plate. Also, a bottom portion of the cartridge may be configured to removably engage with the surgical plate. Additionally or alternatively, the medical device may include an engagement mechanism extending downward from the rigid member to removably engage the cartridge with the surgical plate. If desired, the medical device may include the surgical plate itself, with the plate being a plate through which the screw is extendable.

In another aspect, a method includes extending a screw into a first opening in a cartridge. The first opening is formed at least in part by a non-rigid material, with the non-rigid material configured on the cartridge to stabilize the screw within the cartridge. The method also includes extending the screw through the first opening and into a surgical plate on a patient.

In some examples, the non-rigid material may include silicone and/or thermoplastic elastomer.

In still another aspect, a device includes a cartridge. The cartridge includes a first opening configured to receive a surgical fastener. The first opening is formed at least in part by a non-rigid material configured on the cartridge to stabilize the surgical fastener within the cartridge. The non-rigid material may include silicone and/or thermoplastic elastomer in various examples.

If desired, the device may also include a rigid member engageable with an upper surface of the cartridge. The rigid member may include a second opening that aligns with the first opening for the surgical fastener to pass through the second opening and into the first opening for engagement with the non-rigid material.

Also if desired, the device may include a surgical plate and mechanism for engaging the surgical plate with the cartridge.

The details of the present application, both as to its structure and operation, can best be understood in reference to the accompanying drawings, in which like reference numerals refer to like parts, and in which:

BRIEF DESCRIPTION OF THE DRAWINGS

FIGS. 39A-37E show respective front, top, right side, cross section right, and isometric views of an example H-shape embodiment consistent with present principles;

DETAILED DESCRIPTION

Figure 1:
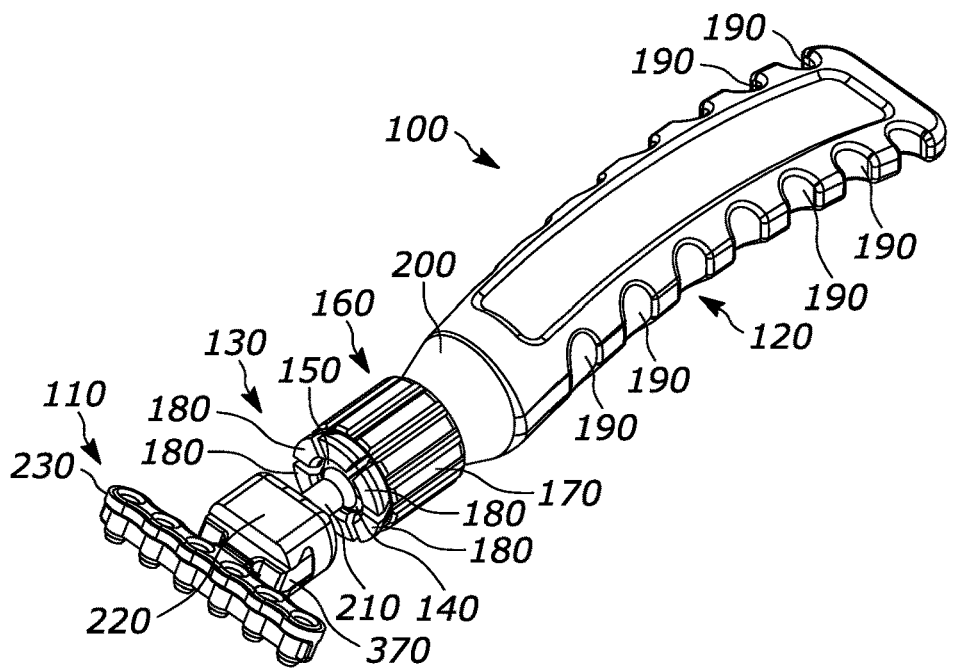
FIG. 1 illustrates a first example embodiment of a medical device in front isometric view consistent with present principles.

Present principles recognize that craniomaxillofacial (CMF) fracture reduction screw handling and driving can be technically improved. However, present principles are not limited to CMF fracture reduction devices and techniques and may also be used in other types of surgical procedures, including other types of open reduction, internal fixation fracture reductions and cranial trauma procedures, cranial reconstruction procedures, and craniotomy procedures. Present principles may also be used in orthopedic procedures not involving the head, including femur fracture reduction, ulna or radius fracture reduction, and others. Present principles may even be used for fastener handling, delivery, and installation in non-medical contexts, including delivering and installing fasteners in carpentry, automotive, mechanical, and assembly/manufacturing contexts.

Accordingly, various example caddies are discussed below. Each caddy can accept and retain CMF and/or neuro screws or other types of fasteners. In some instances, each caddy can even accept and retain a CMF plate, neuro plate, or other type of internal bone fixation plate. Each caddy may be delivered sterile with the plate itself attached to the instrument, whether the plate is a burr hole plate, straight plate, etc. The caddy might even be pre-loaded with 1.5×5 mm screws and/or screws of other sizes. The caddy may allow delivery of the screws into the bone via a driver/blade (e.g., cruciform head screwdriver) while retaining the screws and even the plate itself when accidentally dropped or otherwise jostled.

The caddies may be configured in various shapes to match corresponding plate shapes, with the screw-to-screw distance and arrangement of the screw openings in each caddy being equal to the screw-to-screw distance and arrangement of the screw holes on the respective plate itself. Example shapes include generally rectangular/straight-line hole shapes, rounded burr hole cover shapes, double-Y or dog bone shapes, single-Y shapes, U-shapes, and X-shapes. These caddies may be included as different modular heads that each have a rigid backing/member and non-rigid elastomer material, and the heads can be swapped in and out on a given handle while in the operating room. In some cases, an articulating caddy head may be used so that the head articulates with respect to the handle. Caddies may be configured to accept any desired plate and/or screw for a given procedure.

Additionally, the number of fastener openings that might be included on a given caddy can vary, depending on desired implementation. The fasteners themselves might be self-drilling screws, self-tapping screws, and/or bone screws. The screws may be manual screws or power-driven screws. However, the openings in the caddies may be used for other types of fasteners as well, such as surgical tacks or nails.

The various caddies disclosed herein may also allow adequate visibility to the wound surface, screws, and/or surgical plates. Additionally, the various components of the example devices disclosed below may be manufactured with non-reflective surface finishes (e.g., matte finishes) to reduce glare into the eyes of the surgeon that might otherwise occur due to light reflections from headlamps or other light sources and that could obstruct vision to the surgical site.

In terms of caddy handles, each handle may be assembled with a respective caddy at manufacture or in an operating room. Either way, the handle may be included in a single-use peel packaging that also encloses the caddy, screws, and surgical plate for direct-to-patient delivery.

Caddies consistent with present principles may thus improve the reliability and ease of screw delivery. Caddies consistent with present principles may also improve surgical workflow, allowing for secure multi-screw loading at the back surgical table in situ.

Figure 2:
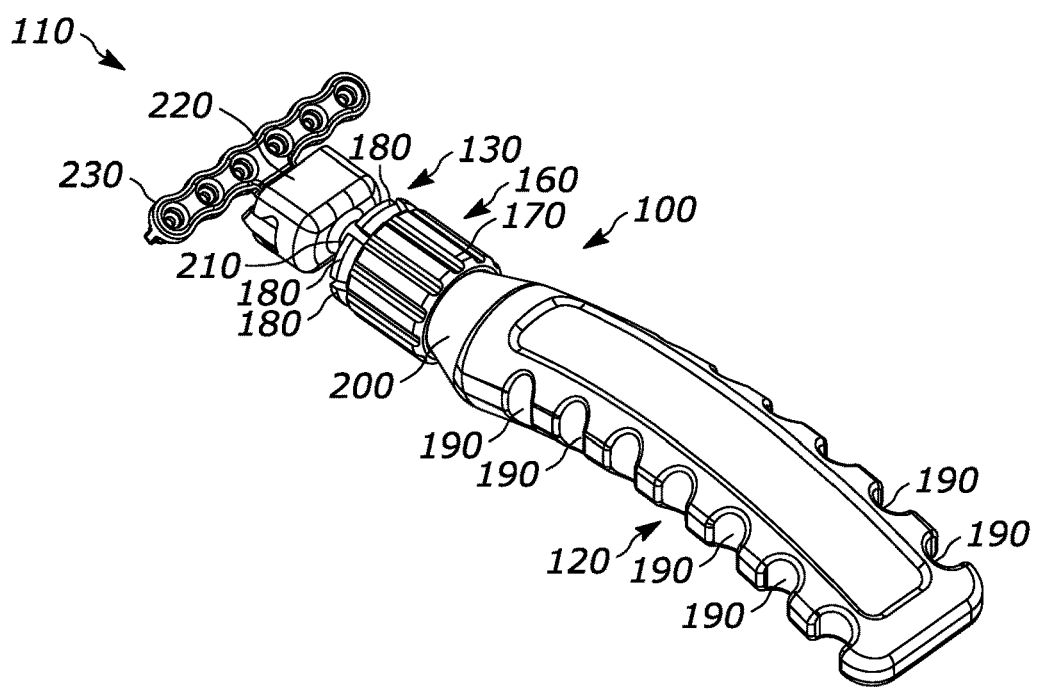
FIG. 2 illustrates the first example embodiment in rear isometric view consistent with present principles.

Now in cross-reference to the front and rear isometric views of FIGS. 1 and 2, an example medical device 100 consistent with present principles is shown. As shown, the device 100 may include a head 110 and elongated, rigid handle 120. The head 110 and handle 120 may be made integral with each other in certain examples, while in other examples the head 110 and handle 120 may be detachable and engageable with each other via a ball and socket joint/assembly 130 (or other mechanism). Either way, the head 110 may attach to the handle 120 with an approximately central axis that extends at an angle between 0 and 90 degrees relative to the long axis of the bone screw(s). The head 110 may be generally rectangular-shaped in the non-limiting example shown. The head 110 may have solid components described in more detail below, along with hollow openings for receiving fasteners such as screws. The cross-sectional shape of the handle 120 may be generally rectangular.

If a ball and socket assembly 130 is to be used, the ball 140 of the ball and socket assembly 130 may be disposed on the head 110 (e.g., made integrally with other portions of the head 110), while the socket 150 of the ball and socket assembly 130 may be disposed on the handle 120, or vice versa. The socket 150 may be established by a spherical opening of a larger diameter than the ball 140.

Additionally, the device 100 may include a locking mechanism 160 to lock the ball 140 into the socket 150 to secure the head 110 on the handle 120 while still allowing articulation of the head 110 with respect to the handle 120. The locking mechanism 160 may be established by a collet 170 and inner teeth/lock ring 180. The teeth 180 may extend longitudinally under the collet 170 according to a longitudinal axis of the handle 120. As shown, the teeth 180 may have protrusions at distal ends nearest the head 110. The protrusions may extend generally inward toward a transverse center of the socket 150 to lock the ball 140 into the socket 150 when the collet 170 is screwed at least partially over top of the teeth 180, while still permitting the ball 140 to rotate within the socket 150 in this locked configuration. The teeth 180 may also be configured to move back and forth toward and away from the transverse center of the socket 150 when the collet 170 is not in the locked position, allowing the ball 140 to pass in and out of the socket 150 to engage or disengage the ball 140 from the socket 150. The teeth 180 may then be locked into place by screwing the collet 170 over the teeth 180, with the protrusions on the teeth 180 creating interference between the ball 140 and teeth 180 that locks the ball 140 within the socket 150, disallowing the ball 140 from passing out of the socket 150 but still permitting articulation of the head 110 with respect to the handle 120.

Thus, note that in some examples outer sidewalls of the teeth 180 may be threaded with female threads to engage male threads on the inside of the collet 170 as the collet 170 is screwed onto the teeth 180, moving the collet 170 distally in the process. Additionally or alternatively, the collet 170 may engage female threads on another portion of the handle to screw the collet 170 onto the teeth 180. Either way, also note for completeness that the teeth 180 may be configured to abut each other in close interference fit in the locked configuration in some examples, while in other examples adjacent teeth 180 may still be radially spaced apart from each other as shown in FIG. 1.

Figure 3:
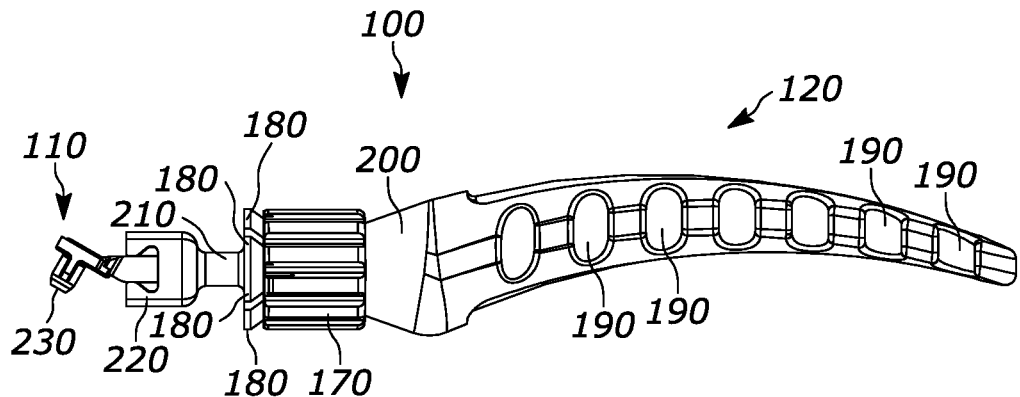
FIGS. 3 and 6 illustrate the first example embodiment in left side elevational views according to unlocked and locked configurations consistent with present principles.
Figure 4:
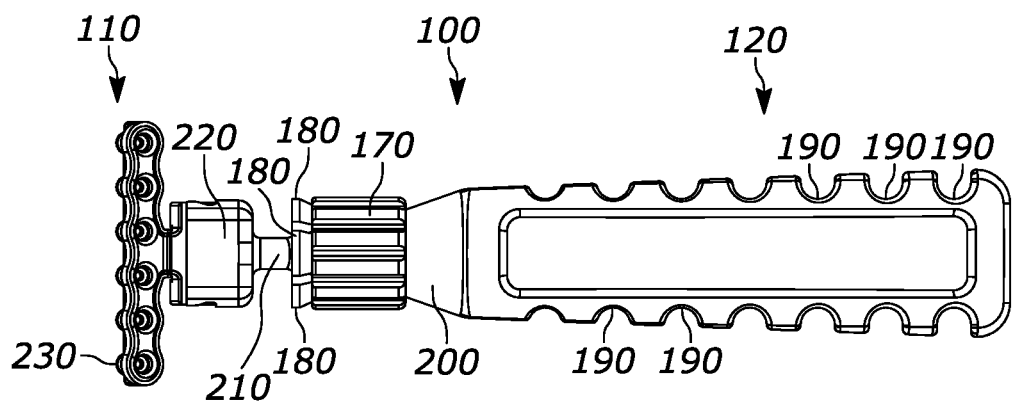
FIGS. 4 and 7 illustrate the first example embodiment in bottom plan views according to unlocked and locked configurations consistent with present principles.
Figure 5:
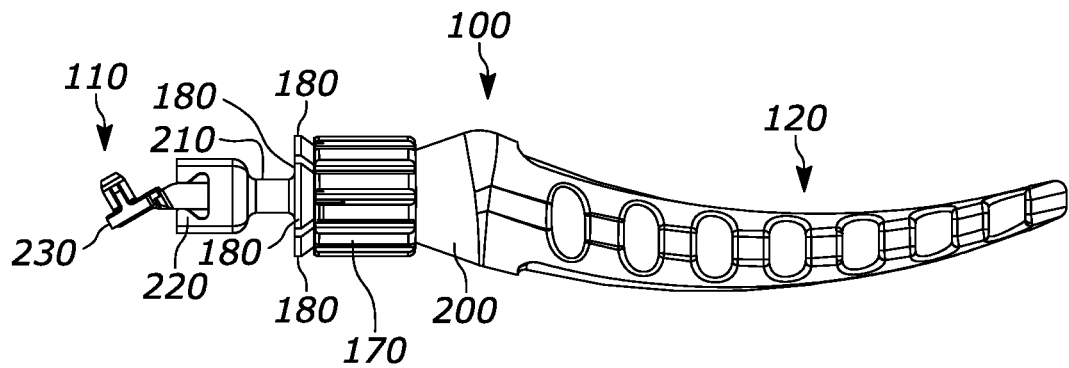
FIGS. 5 and 8 illustrate the first example embodiment in right side elevational views according to unlocked and locked configurations consistent with present principles.
Figure 6:
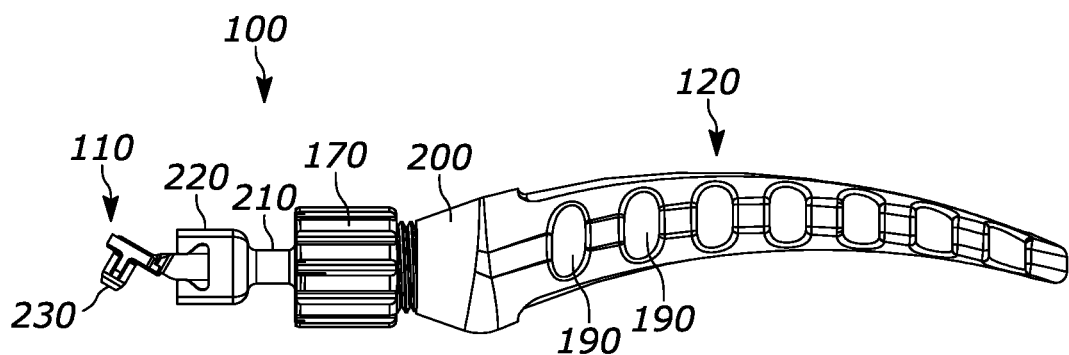
Figure 7:
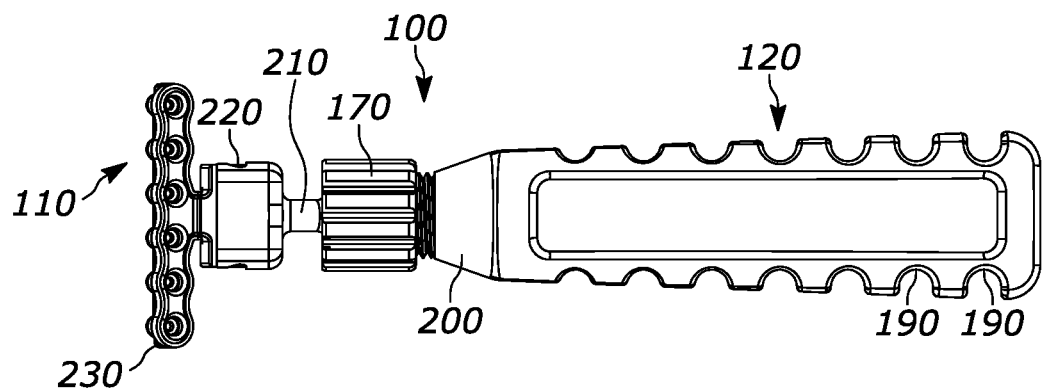
Figure 8:
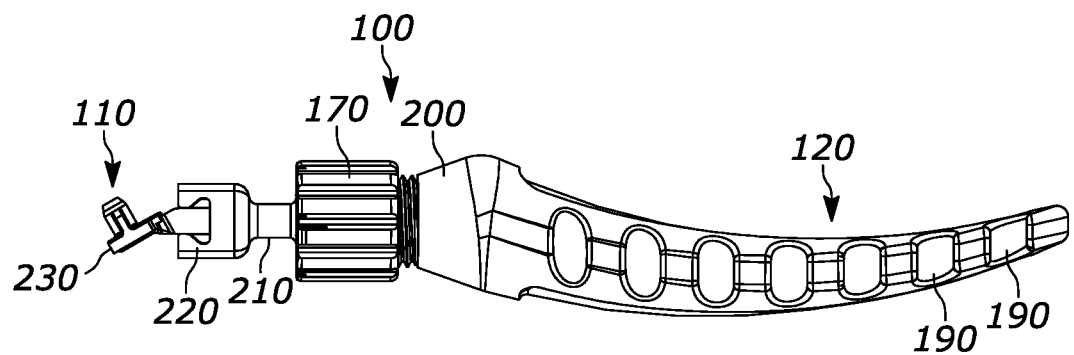

FIGS. 3-5 show the mechanism 160 in unlocked configuration respectively in left side elevational, bottom plan, and right side elevational views. FIGS. 6-8 then show the mechanism 160 in locked configuration respectively in left side elevational, bottom plan, and right side elevational views. Note per FIGS. 3-5 that the collet 170 is located more proximal to the body of the handle 120 while the mechanism 160 is unlocked, and more distally away from the body of the handle 120 while the mechanism 170 is locked per FIGS. 6-8 (after being rotationally screwed down onto and over top of the teeth 180).

Now referring back to FIGS. 1 and 2 and describing the handle 120 in more detail, it may be arced or bowed in the transverse dimension as shown, with an apex of the arc or bow being located at a midway point of the handle 120 according to the longitudinal dimension. Therefore, as shown in these figures, the arc or bow may extend transversely upward relative to a top surface of the handle 120. The handle 120 may also have one or more grooves 190 for ergonomic hand gripping by a surgeon. Also note that a distal portion of the handle 120 establishes a collar 200 that slopes inward distally until it engages proximal inner surfaces of the collet 170 to couple the collet 170 to the rest of the handle 120.

Now describing the head 110 in more detail, note that an arm 210 on the head 110 may be integral with the ball 140 and extend distally away from the ball 140. An opposing, distal end of the arm 210 may engage a clamp or holder 220 on the head 110. The holder 220 may have a distal opening as shown to receive a cartridge assembly/caddy 230 consistent with present principles.

Figure 9:
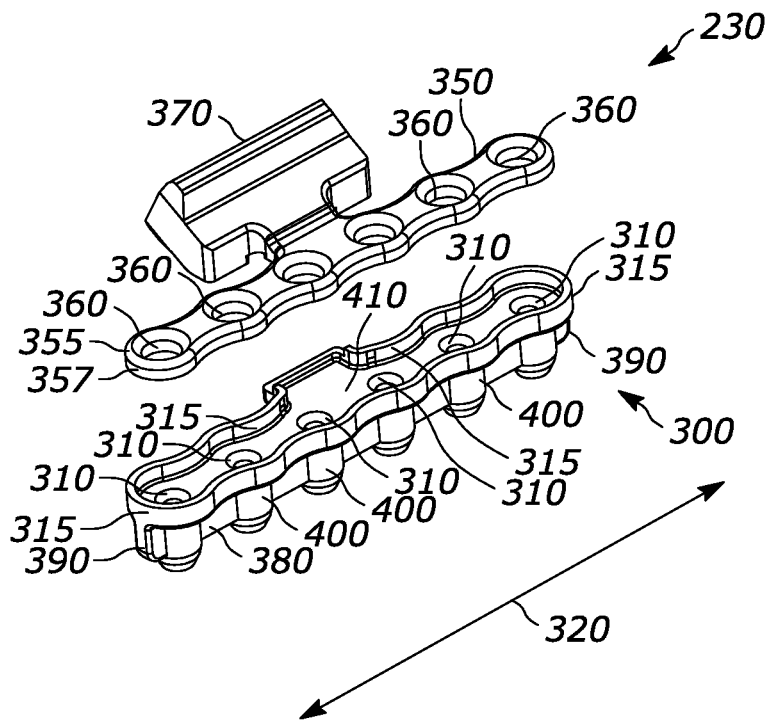
FIG. 9 shows an example non-rigid cartridge and example rigid member in exploded isometric view consistent with present principles.

Now in reference to FIG. 9, the cartridge assembly/caddy 230 is shown in greater detail in exploded upper isometric view. As shown, the assembly/caddy 230 may include a cartridge 300. The cartridge 300 may be radiolucent for the surgeon to visualize screw trajectory. The cartridge 300 may be smooth on the outside. The cartridge 300 may also be soft and pliable/flexible yet resilient due to the non-rigid elastomer with which it is constructed, able to deform when a screw passes through but still able to resume a preconfigured size and shape after the screw passes through.

The cartridge 300 may be solid but include one or more first openings 310 that are each configured to receive a respective screw or other fastener. The first openings 310, and indeed some or all of the cartridge 300 itself, may be formed using the non-rigid material. The non-rigid material may be an elastomer such as silicone alone, rubber alone, thermoplastic elastomer (TPE) alone, a combination of silicone and/or rubber and/or thermoplastic elastomer, or a combination of silicone/rubber/thermoplastic elastomer and other material. In one specific non-limiting example, thermoplastic polyurethane (TPU) may be used, while in another non-limiting example elastic medical-grade liquid silicone rubber (LSR) may be used.

The composition of the non-rigid elastomeric material, along with its arranged structure on the cartridge 300 as described in greater detail below, help to stabilize the screws (or other fasteners) within the first openings 310 of the cartridge 300, also allowing the screws to still be moved independently of each other while each screw is still in a respective opening 310. One screw at a time may then be aligned with a hole in a surgical plate for the screw to then be screwed through the respective opening 310 and into the surgical plate (and hence patient), or multiple screws may be concurrently aligned with holes on the plate to then keep the cartridge 300 immobile with respect to the plate as different screws are progressively screwed in via the openings 310.

As also shown in FIG. 9, the openings 310 in this example may form a single row, with the openings 310 being linearly aligned with each other and spaced apart from each other in a transverse dimension (labeled 320 in FIG. 9) to establish a linear opening configuration. In other examples, multiple rows of openings 310 may be included on the cartridge 300 to establish a rectangular hole configuration. Other hole configurations are also encompassed by present principles, including a circular/burr hole configuration, a double-Y or dog bone configuration, a single-Y configuration, etc.

FIG. 9 also shows that the assembly/caddy 230 may include a rigid member 350. In the example shown in FIG. 9, a distal portion of the rigid member 350 may be transversely elongated left to right. The member 350 may be engaged/engageable with one or more upper surfaces of the cartridge 300. The upper surfaces of the cartridge 300 may include outer sidewalls and/or inner sidewalls 315 of the cartridge 300 that extend up from a top face 410 of the cartridge, and/or the top face 410 itself, for example. The rigid member 350 may include edges 355 tapering outward and downward to sidewalls 357. In one specific instance, the lower portions of the rigid member 350, including the sidewalls 357, may be reciprocal with and seated within the open-top bay created by the upper sidewalls 315 and top face 410 of the cartridge 300 (the bay best shown in FIG. 9) to engage the cartridge 300 with the member 350. The edges 355 and sidewalls 357 may be bulbous in the proximal-distal plane, undulating between bulbed portions that surround each respective second opening 360 as located on the member 350 and described in more detail later.

Figure 10:
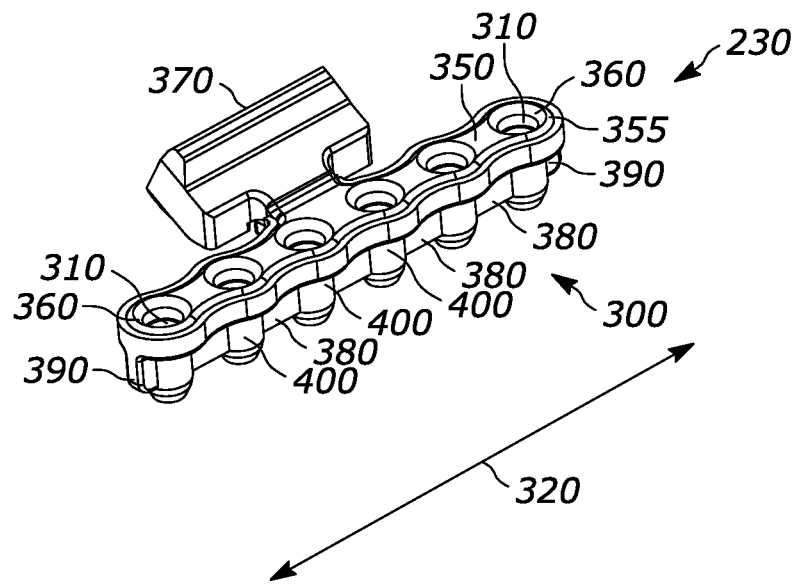
FIG. 10 shows the cartridge assembly in upper isometric view consistent with present principles.

FIG. 10 therefore shows the cartridge 300 and rigid member 350 coupled to each other via snap fit or interference fit of the member 350 within the cartridge's bay. Note that in the example shown, the rigid member 350 covers most if not all of the top face 410 of the cartridge 300.

In addition to or in lieu of snap or interference fit, the cartridge 300 and member 350 may be inseparably bonded together using an adhesive/glue at manufacture (inseparably bonded save for the combined assembly itself being broken/deconstructed). As another example, the non-rigid elastomeric material (e.g., TPE, silicone and/or other elastomer) of the cartridge 300 may be over-molded onto the member 350 at manufacture so that the two components are inseparably bonded (again save for the combined assembly itself being broken/deconstructed).

The member 350 may be established by a rigid metal such as medical-grade steel or aluminum, for example. Additionally or alternatively, the member 350 may be established by a hard plastic and/or other hardened polymer. As referenced above, the member 350 may also have a matte finish or other non-reflective finish to minimize any glare off the member 350 in a surgical environment.

Still in reference to FIGS. 9 and 10, as mentioned above the distal portion of the rigid member 350 may include one or more second openings/counterbores 360. The openings 360 may vertically align with respective first openings 310 on the cartridge 300 for a respective screw to pass vertically through a respective second opening 360 and into an aligned first opening 310 for engagement of the screw with the non-rigid material of the cartridge 300.

As also shown in FIGS. 9 and 10, the rigid member 350 may be made integral with or otherwise coupled to a rigid male dovetailed element 370 extending proximally away from the cartridge 300 to meet the holder 220. The element 370 may be made of the same rigid metal or other material as the rest of the member 350. In the particular example shown, the element 370 may transversely slide into a reciprocal distal opening on the holder 220 from either side, mating the cartridge 300 and member 350 with other portions of the head 110 and/or handle 120. Thus, as also shown in these figures, the element 370 may include protrusions extending upward and downward, even sloping proximally upward and downward from a main body portion of the element 370, to mate with the reciprocal distal opening on the holder 220. The element 370 may thus closely engage the holder 220 in interference and/or friction fit, providing added stability and immobility of the element 370 and member 350 with respect to the holder 220.

Figure 11:
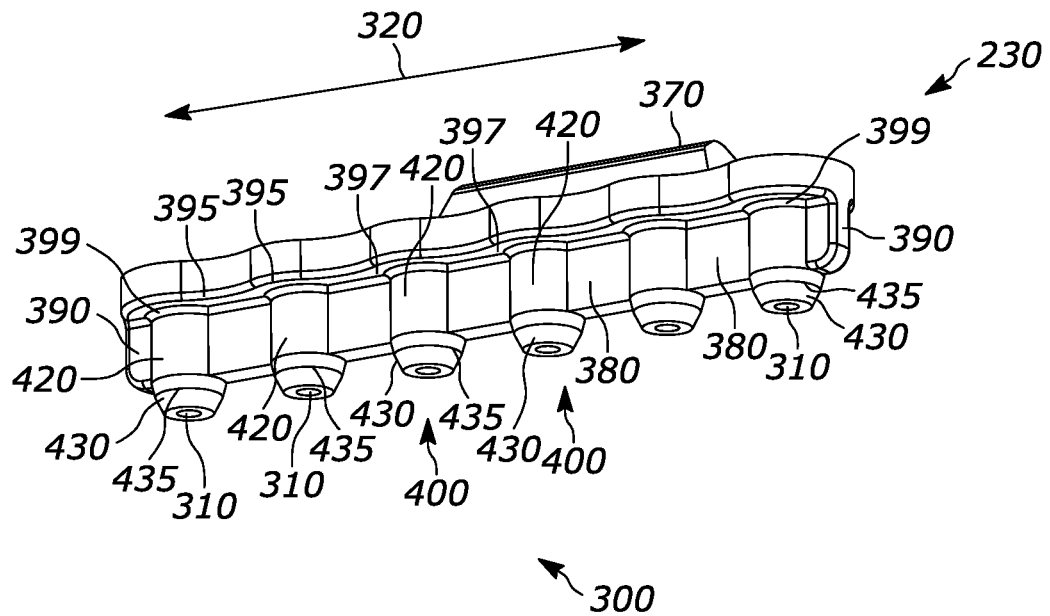
FIG. 11 shows the cartridge assembly in lower isometric view consistent with present principles.

Turning to FIG. 11, this figure shows a bottom isometric view of the assembly 230 as it might have been sterilely assembled at a factory or other facility prior to being provided to healthcare professionals. As shown, the non-rigid cartridge 300 may include non-rigid connectors/ribs 380 that are formed integrally with and located between the generally cylindrical portions 400 of the cartridge 300 that themselves establish the openings 310 (e.g., as formed through injection molding, 3D printing, etc.). The connectors 380 may be parallelepiped in shape, such as rectangular box-shaped. The connectors 380 may be included to add stability and structural integrity to the cartridge 300, providing some rigidity upon screw insertion into the openings 310.

Further note that side arms 390 may also be formed integrally with the outer-most cylindrical portions 400 on each side of the cartridge 300 as shown, also for stability and structural integrity. In some examples, the side arms 390 may be rounded or taper inward at the lower ends as shown. Note that lower surfaces 395 of the upper sidewalls 315 may taper down to a flat horizontal surface 397. Additionally, tapering walls 399 may extend proximally downward from the surface 397 to meet both vertical sidewalls of the cylindrical portions 400 and the sidewalls of the connectors 380.

As for the generally cylindrical portions 400 of the cartridge 300 that establish the openings 310, they may include a respective cylindrical upper chamber 420 that is proximal to the rigid member 350 and integral with the horizontal structure of the cartridge 300 forming the top face 410. Thus, the top face 410 may be perpendicular to the longitudinal axes of the cylindrical upper chambers 420.

Distal to the cylindrical upper chambers 420, the exterior surface of each respective portion 400 may taper distally inward at a respective distal end portion 430 to receive a respective hole of a surgical plate. In some specific implementations, each end portion 430 may also include a raised rib 435 midway down the portion 430, with the rib 435 circumscribing the end portion 430 perpendicularly to the longitudinal/vertical axis of the respective chamber 420. The rib 435 may be included to add further stability and structural integrity to each opening 310 and providing added rigidity during screw insertion.

To reiterate, the connectors 380 and portions 400 may be made of LSR, TPE, and/or other non-rigid elastomeric material as set forth above. The tapering distal end portions 430 may therefore be gently positioned to extend at least partially into aligned holes on the surgical plate itself without undue jostling or force that might translate to the patient. The non-rigid, pliable (yet resilient) characteristics of the non-rigid material also advantageously allow a screw with a slightly larger screw shaft diameter (larger than the diameter of the respective opening 310) and larger-diameter screw head to still be driven through the portion 400 and into the hole in the surgical plate in a stable, controlled manner during fracture reduction.

The rigid nature of the rigid member 350 also lends its own advantages, since control of it via the handle 120 allows the screws to be driven through the openings 310 in the cartridge 300 under adequate hand control without undue action in the non-rigid material. The rigidness of the rigid member 350 also allows the screwdriver or driving blade to be removed from the assembly 230 without adhering to the non-rigid material or screw itself, reducing the chance of undue and unintended force being translated to the patient at or near the fracture site. Thus, in one specific example, the screwdriver may be separated from the screw by toggling the driver bit at an acute angle and lifting the driver away from the screw head once disengaged.

What's more, in some examples the tapering distal end portions 430 of the cartridge 300 may be configured to removably engage the surgical plate using a plate engagement mechanism, coupling the surgical plate to the cartridge 300 and indeed the device 100 itself so that the entire assembly can be transported from a back surgical table to the patient as a single unit (with screws already loaded into the openings 310). The assembly including bottom surgical plate may then be aligned with a fracture site of the patient as desired. This allows the cartridge assembly 230 to remain locked and immobile with respect to the plate so that the plate may be placed on the patient where desired and then the screws may be screwed into the plate/patient through the assembly 230 one at a time without the assembly 230 or screws needing to be realigned each time the surgeon moves from one screw to another on the assembly 230.

Figure 12:
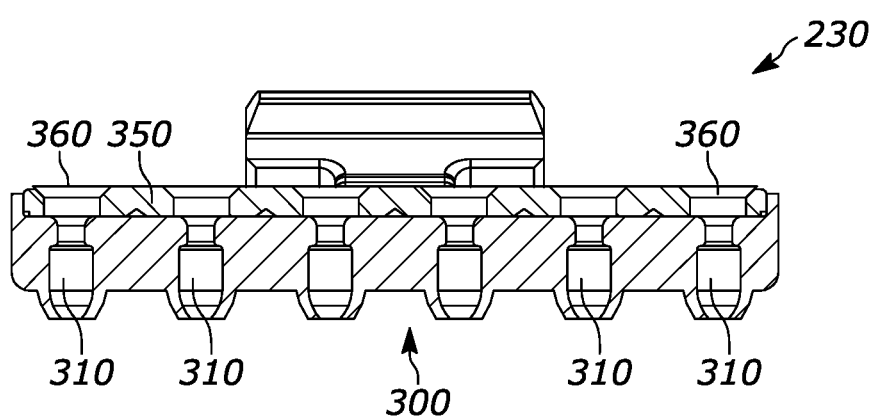
FIG. 12 shows the cartridge assembly in front cross-section view consistent with present principles.

Now in reference to FIG. 12, a front elevational view of the cartridge assembly 230 is shown. Note that certain outer front surfaces of the cartridge 300 are shown transparently for illustration to demonstrate the inner structure of the first openings 310 on the cartridge 300 and aligned second openings 360 on the rigid member 350. As may be appreciated from FIG. 12, the openings 310 may establish inner open chambers to closely receive surgical screws.

Figure 13:
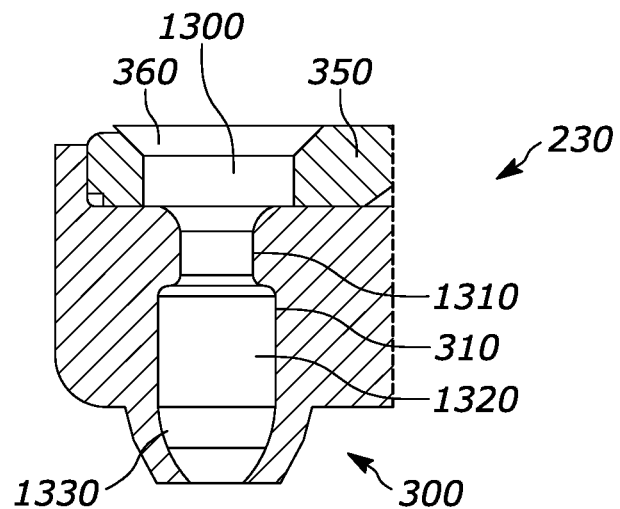
FIG. 13 shows a close-up cross-section view of part of the cartridge assembly as also shown in FIG. 12.

The structure of the openings 310 and 360 may be further appreciated from FIG. 13, which shows a close-up front view of the left-most openings 310/360 shown in FIG. 12. As shown in FIG. 13, the opening 360 may include a cylindrical/disc-shaped open area 1300 in which the head of the screw may sit (e.g., flush or sub-flush to the top surface of the rigid member 350) when the screw is disposed within the cartridge 300. Beneath the area 1300, the opening 310 may connect and taper inward into a cylindrical retention neck/bottleneck 1310 to retain the screw, with the bottleneck 1310 having a lesser diameter than the disc-shaped area 1300. Recognizing that in certain non-limiting examples an average CMF surgical screw shaft width might be between 1.0 mm and 1.6 mm, the diameter of the bottleneck 1310 may be 0.8 mm to 1.0 mm. The non-rigid material at the bottleneck 1310 is therefore able to expand to receive the screw shaft, stabilizing the screw in the process owing to the interference fit.

FIG. 13 also shows that the bottleneck 1310 may then taper outward at a lower/distal end toward a cylindrical chamber 1320 of the opening 310. The chamber 1320 may have a wider diameter than the bottleneck 1310, and in some examples the diameter of the chamber 1320 may be wider than the outer limit of average-diameter CMF surgical screw shafts. As such, the diameter of the chamber 1320 may be 1.7 mm to 2.0 mm in non-limiting examples. Note further that the diameter of the chamber 1320 may still be less than the diameter of the area 1300 and head of the surgical screw itself so add further stability as the screw head passes through the chamber 1320 and into the plate/patient.

Accordingly, as the screw is driven into the patient, the screw shaft will be initially stabilized in the bottleneck 1310 while threading into the patient begins (before additional support is provided via the bone structure itself). As driving continues, the bottleneck 1310 may expand even further to allow the screw head to pass therethrough, stabilizing the screw head in the process. Then as the patient's bone structure/screw interface begins providing additional screw stabilization during driving, the head of the screw may pass into and through the chamber 1320 where, owing to less interference/lateral force existing between the screw head and chamber 1320 compared to the force exerted by the bottleneck 1310, the screw may be more easily driven into the patient. Thereafter, the screw head may pass through a tapering funnel 1330 of the opening 310, with the funnel 1330 formed inside the distal end portion 430.

It may thus be appreciated that the structure of the opening 310 is optimized for both stabilization early in screw driving and ease of driving later in screw driving (of the same screw). The funnel 1330 may then provide greater interference/pressure on the screw head at the end of driving, allowing the cartridge 300 to stay in position without becoming dislodged from the plate so that the surgeon can then drive another pre-loaded screw through another opening 310 as might already be aligned with another hole on the same surgical plate.

Figure 14:
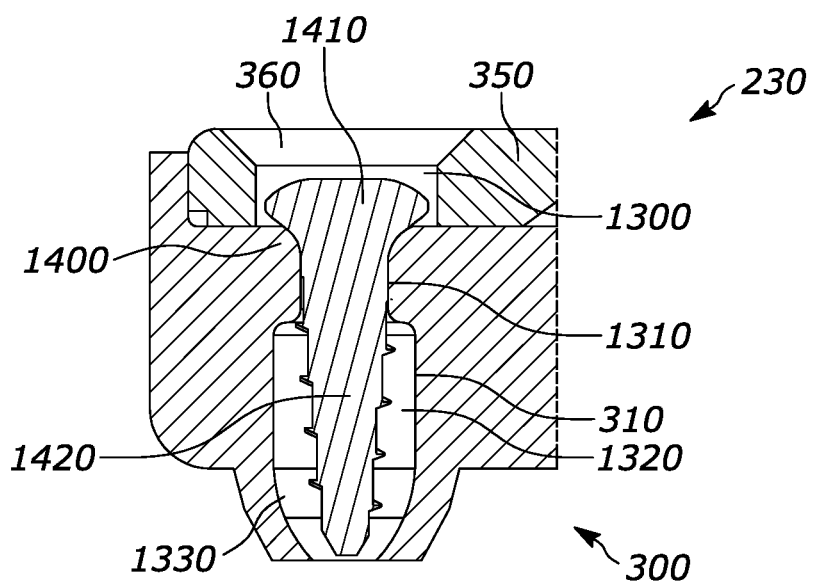
FIG. 14 shows a close-up cross-section view of the cartridge assembly with a screw inserted into the cartridge consistent with present principles.

FIG. 14 therefore shows an example where a surgical screw 1400 (with head 1410 and shaft 1420) has been pre-loaded into a respective opening 310 of the cartridge 300 for subsequent driving into a patient per the above. The position of the screw 1400 within the openings 310/360 as shown in this figure may establish the positioning of the screw 1400 as pre-loaded at manufacture and/or at a back surgical table of an operating room before transport to the fracture site of the patient.

Figure 15:
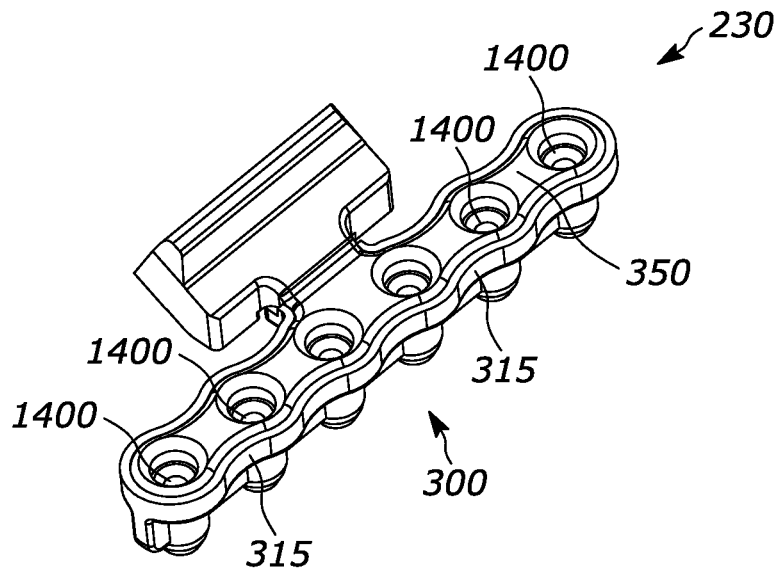
FIG. 15 shows an upper isometric view of the cartridge assembly with screws loaded consistent with present principles.

FIG. 15 shows an upper isometric view of the cartridge assembly 230 with the cartridge 300 and rigid member 350 coupled to each other and with screws 1400 pre-loaded into the openings 310. It may be appreciated from FIG. 15 that the geometry of the assembly 230 allows adequate surgeon visibility to the wound surface (e.g., through the scalloped indents in the sidewalls 315).

Figure 16:
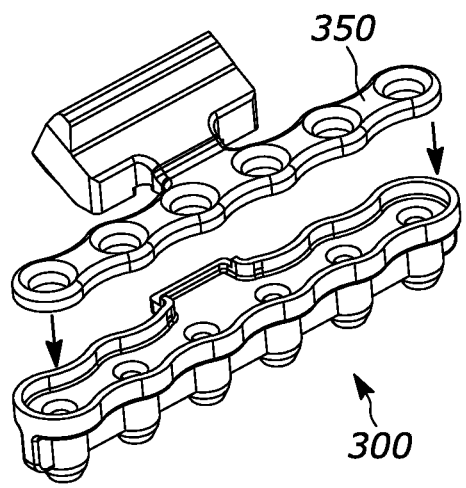
FIGS. 16-19 graphically illustrate different steps that may be taken to assemble the first example embodiment consistent with present principles.
Figure 17:
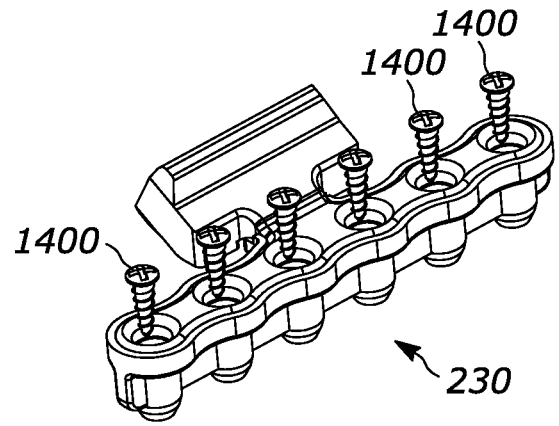
Figure 18:
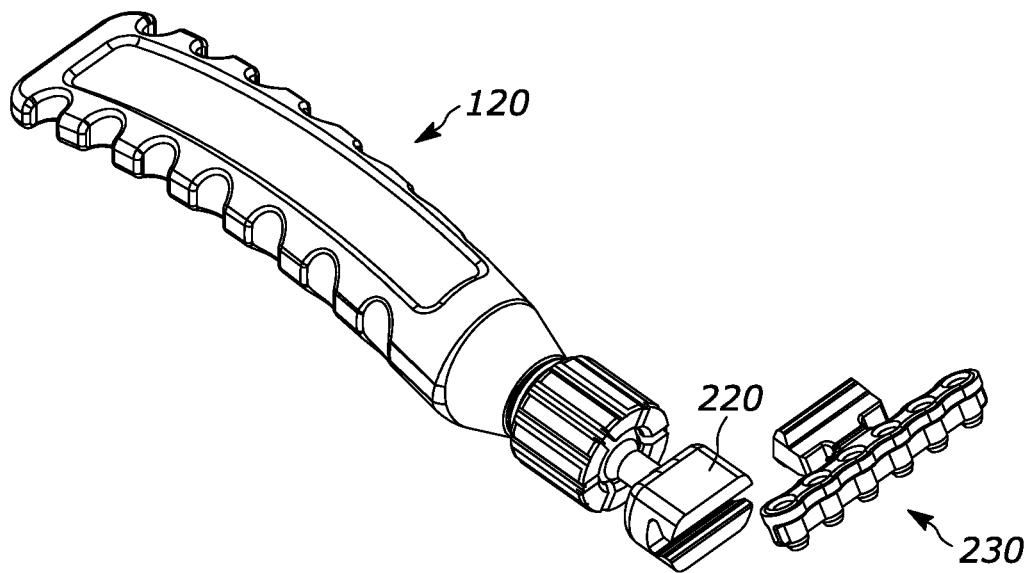

FIGS. 16-19 show example steps for assembling the device 100 at a back surgical table of an operating room during a CMF fracture reduction procedure. As shown in FIG. 16, the rigid member 350 may be engaged with the cartridge 300 if not already, with it being further recognized that in non-limiting examples the rigid member 350 and cartridge 300 may already be inseparably bonded together at manufacture. FIG. 17 then shows that after engagement, the screws 1400 may be loaded into the openings 310. FIG. 18 then demonstrates that the cartridge assembly 230 may be slidably engaged with the holder 220 as described above.

Note here that while these three steps might be performed by medical professionals in an operating room, in other instances one or more of these steps may be performed in a sterile manufacturing facility during manufacture of the device 100. For example, the assembled cartridge assembly 230 and pre-loaded screws 1400, possibly as themselves loaded onto the rest of the device 100, may be sterilely packaged together at manufacture and then sold (or otherwise provided) to the medical professionals in advance of a CMF fracture reduction procedure or other type of procedure for which the device 100 is to be used.

Figure 19:
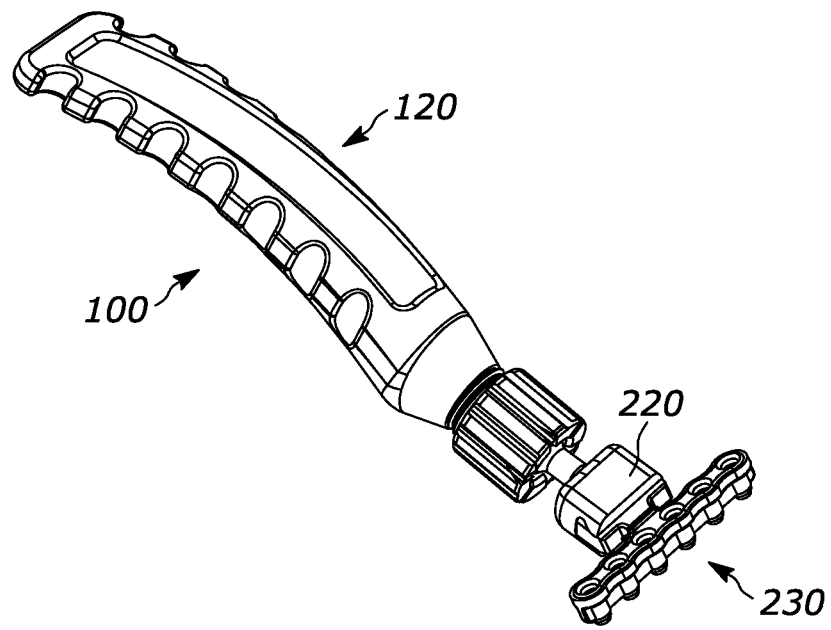
Figure 20:
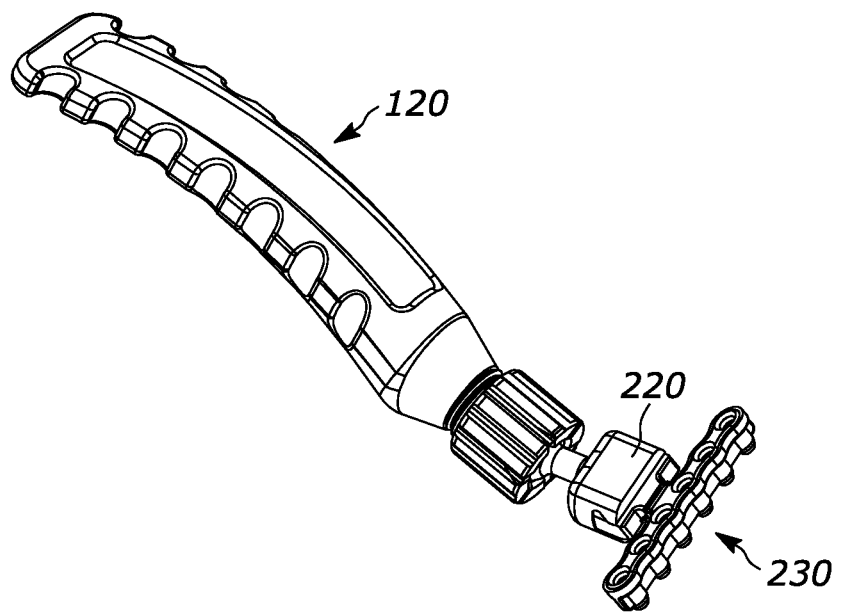
FIGS. 20 and 21 graphically illustrate articulation of the device's head with respect to the device's handle consistent with present principles.
Figure 21:
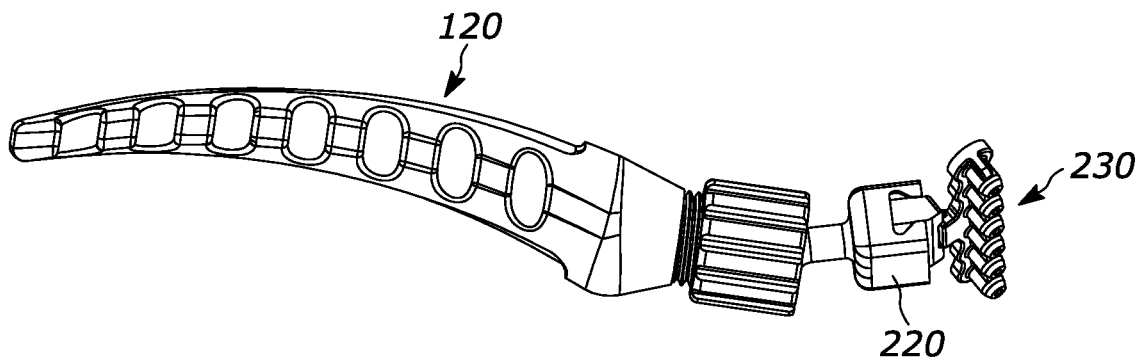

FIG. 19 therefore shows the assembled device 100 with screws pre-loaded. The upper isometric view of FIG. 20 and side elevational view of FIG. 21 then show that, owing to the ball and socket assembly 130 (in its locked position) allowing the assembly 230 to articulate radially about a longitudinal axis of the socket 150 and/or handle 120, the assembly 230 may be rotated to the left and right as shown.

Figure 22:
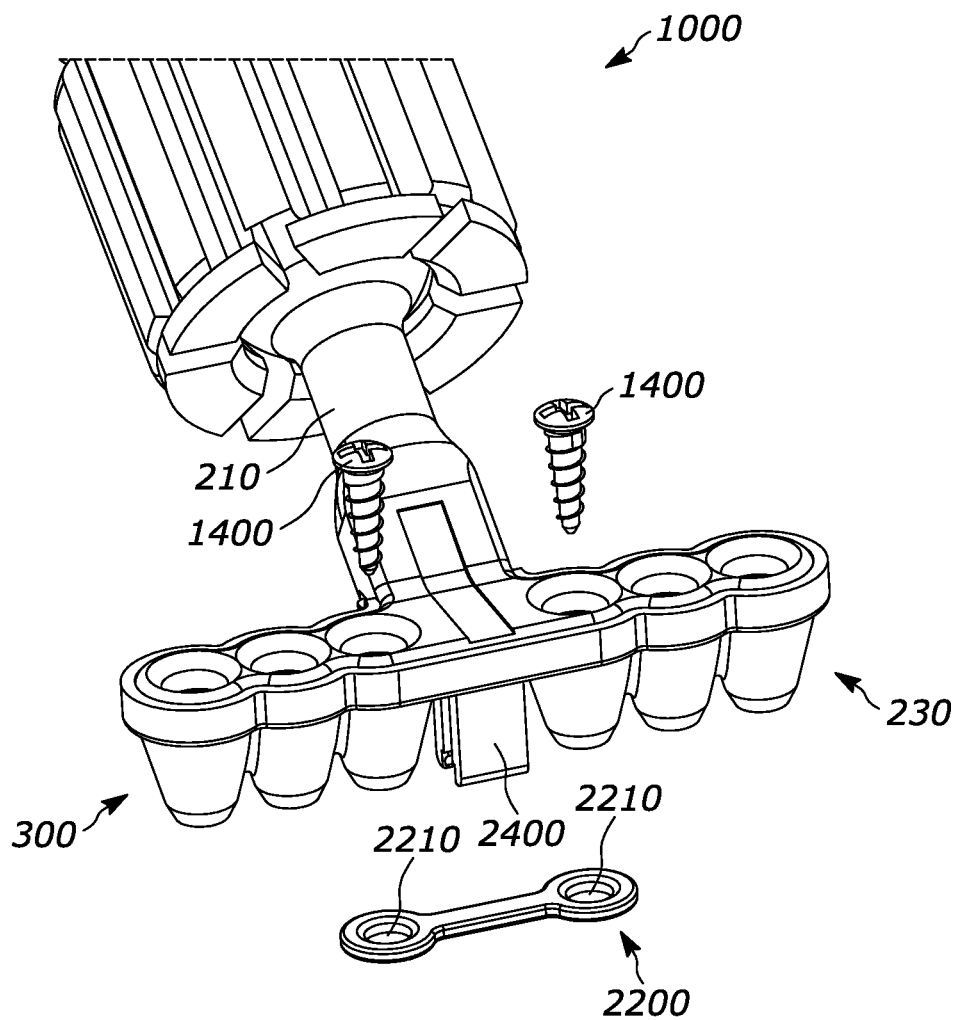
FIG. 22 shows a second example embodiment of a medical device in upper isometric view consistent with present principles.
Figure 23:
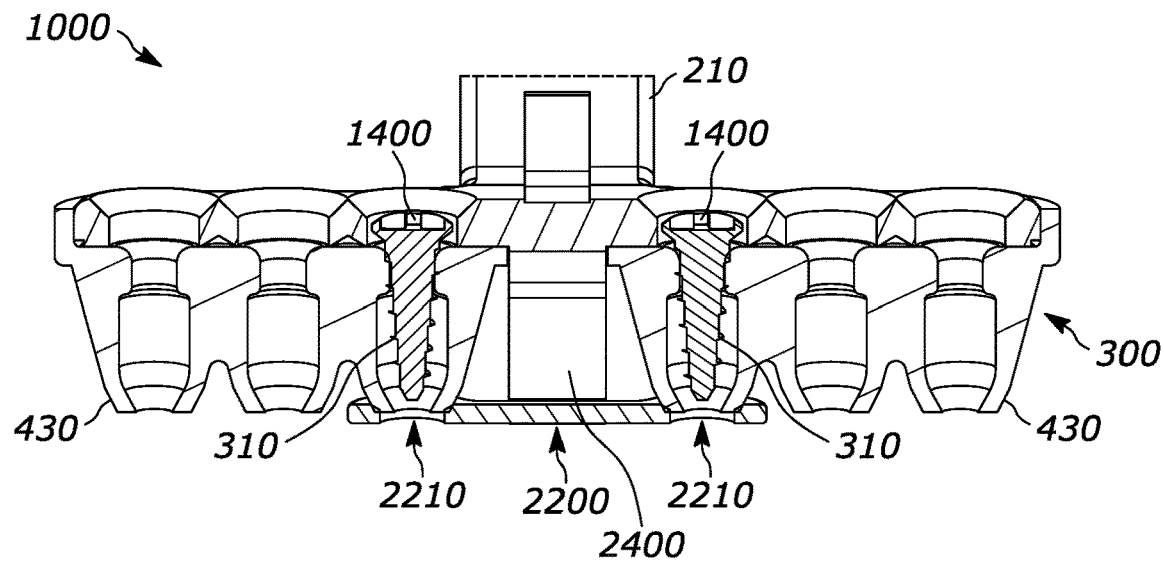
FIG. 23 shows the second example embodiment in front cutaway cross-section view consistent with present principles.

FIG. 22 shows an isometric view of an example where a device 1000 consistent with present principles is loaded with screws 1400. A straight-hole H-plate 2200 is also shown as being located nearby. The front cutaway view of FIG. 23 then shows that certain openings 310 in the cartridge 300 may be aligned with respective holes 2210 in the plate 2200. The tapered distal end portions 430 of the cartridge 300 may thus nest into the counterbores on the bone plate 2200 to help locate and extend each screw 1400 into the desired plate hole. Each tapered distal end portion 430 may thus be progressively aligned into a respective plate hole one screw at a time, or multiple distal end portions 430 may be simultaneously aligned with different holes in the plate 2200.

Figure 24:
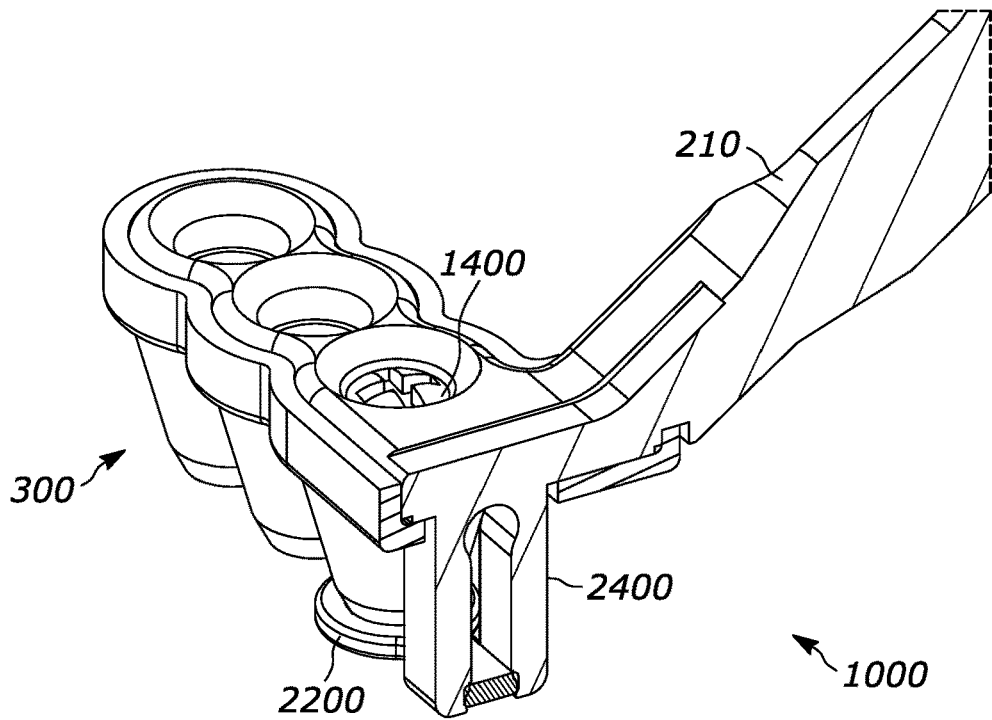
FIG. 24 shows the second example embodiment in side cutaway cross-section isometric view consistent with present principles.

The side cutaway isometric view of FIG. 24 then demonstrates that a fork, vice, clip, tangs, cam levers/cantilever arms, or other plate engagement mechanism 2400 may extend downward from the middle of the rigid member 350 to engage a neck of the plate 2200 between the holes 2210, removably engaging the plate 2200 with lower distal end portions of the cartridge 300 and indeed device 1000 itself for the device 1000 with plate 2200 to be subsequently aligned with the fracture site of a patient as a single unit. The mechanism 2400 may be integral with the member 350 if desired and made of the same material (e.g., aluminum).

Also note here that according to this example, the arm 210 itself has been formed integral with the rigid member 350 as a unitary element (e.g., using aluminum or another rigid material mentioned above for the element 350). This example embodiment may therefore omit the element 370 and holder 220. FIG. 24 also shows that the distal ends of the fork or vice 2400 may include a step inward on inner surfaces as shown to closely receive the neck of the plate 2200. If desired, a rachet or other clamping mechanism located elsewhere on the device 1000 may then be used to clamp the plate 2200 within the fork or vice 2400, exerting lateral force on the plate 2200 to hold the plate 2200 in place.

Figure 25:
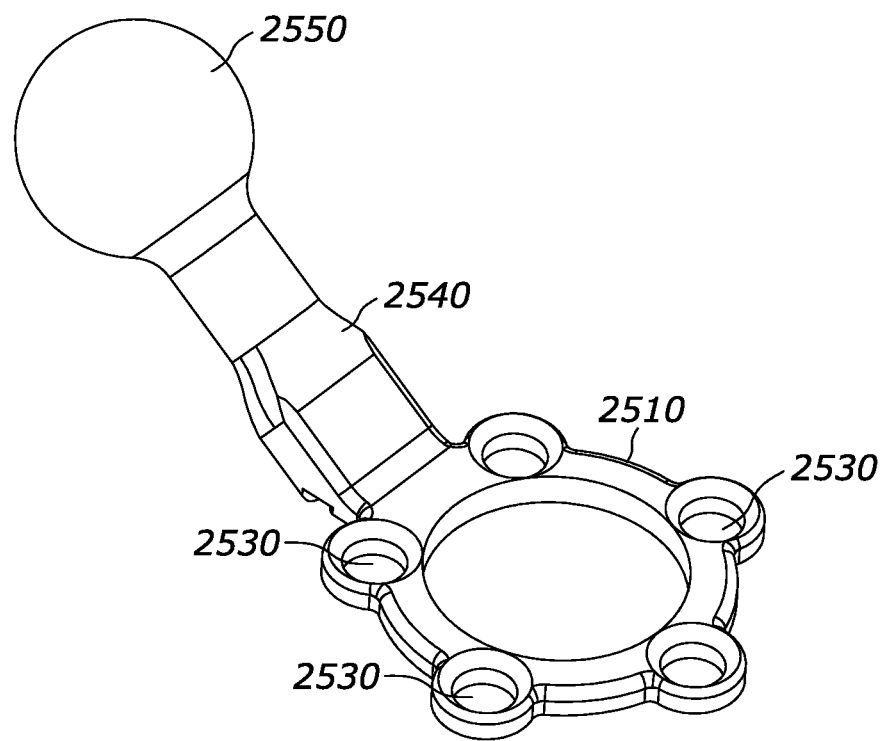
FIGS. 25-27 show upper isometric views of a third example embodiment of a medical device in upper isometric view in various stages of assembly consistent with present principles.
Figure 25:
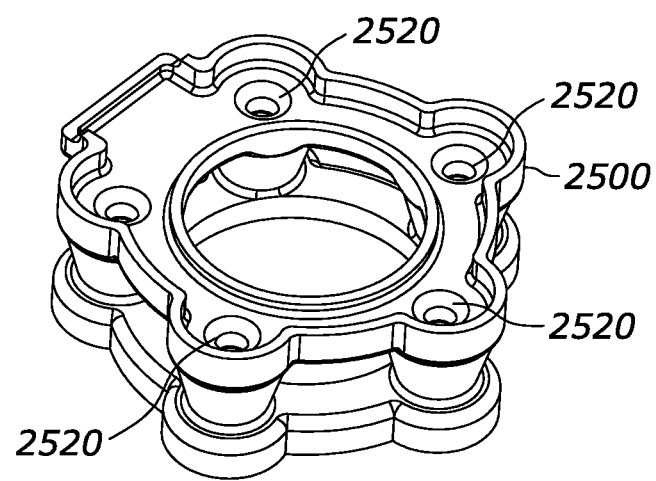
Figure 26:
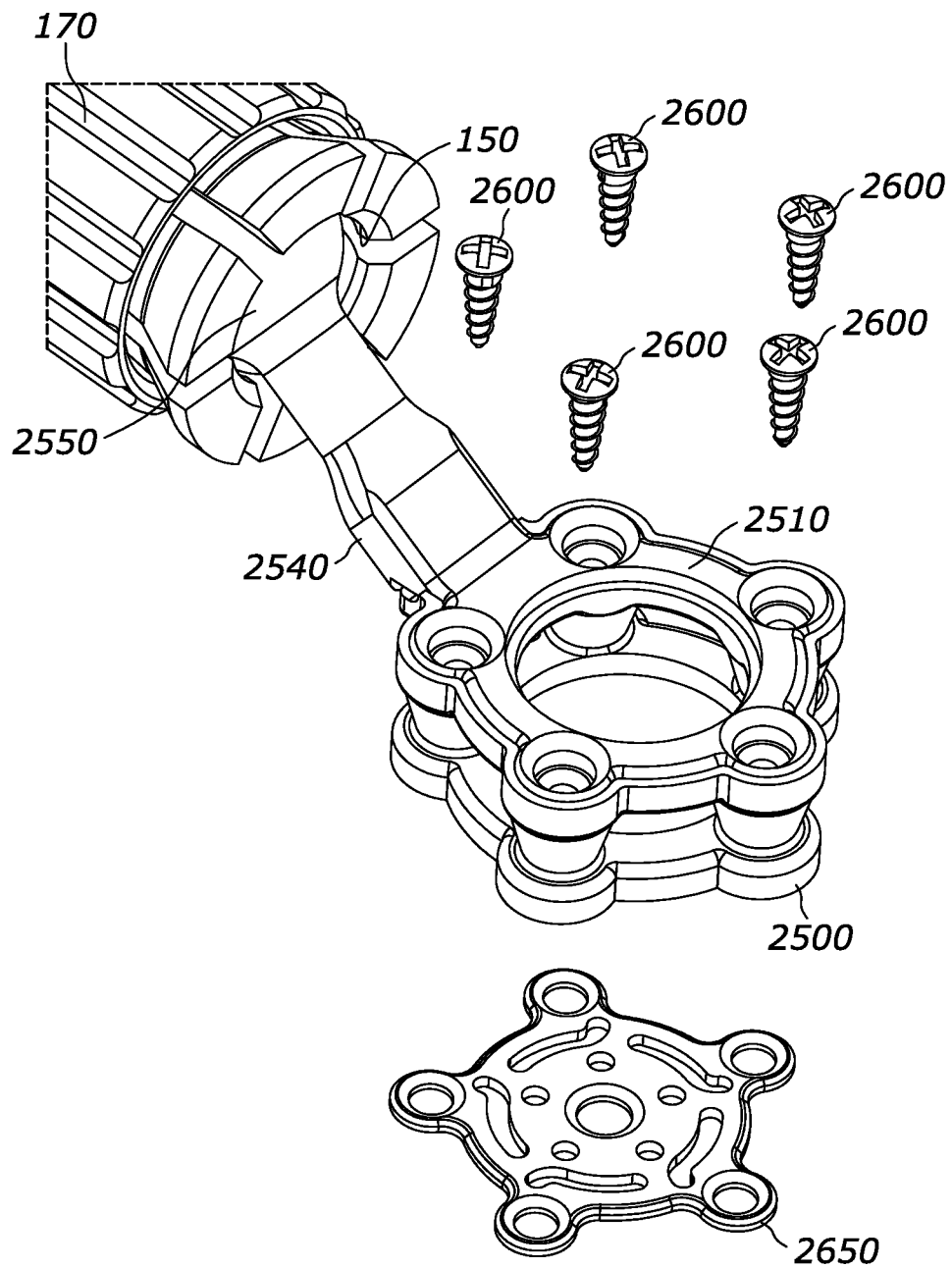

FIGS. 25 and 26 show another example embodiment consistent with present principles. Here, a cartridge 2500 (e.g., silicone/TPE) and rigid member 2510 (rigid metal backing) are shown together as a caddy. Save being generally circular/cylindrical as shown, the cartridge 2500 may be similar in function and configuration to the cartridge 300 and the rigid member 2510 may be similar in function and configuration to the rigid member 250. As such, the cartridge 2500 may include first openings 2520 similar to the first openings 310 discussed above, while the rigid member 2510 may include second openings 2530 similar to the second openings 360 discussed above.

FIGS. 25 and 26 also show that the rigid member 2510 may be made integral with an arm 2540 extending back to a ball 2550. FIG. 26 shows that the ball 2550 may be received into the socket 150 on the handle 120 for locking therein via the collet 170. Note that the arm 2540 may be formed with the member 2510 as a unitary element, and as such the arm 2540 may be made of aluminum, steel, and/or another rigid material.

FIG. 26 also shows that screws 2600 may be inserted through respective vertically aligned openings 2520/2530 and into a surgical burr hole plate 2650 that has reciprocal holes through which the screws 2600 may be threaded to thereby couple the plate 2650 to the assembly 2500/2510.

Additionally or alternatively, the plate 2650 may be coupled to the assembly 2500/2510 through a boot or bay on a bottom portion of the cartridge 2500, establishing another type of plate engagement mechanism but established by the non-rigid elastomer of the cartridge 2500 itself. The boot or bay may therefore be integral with other portions of the cartridge 2500, formed by downward cartridge sidewalls and a flat, horizontal, downward-facing surface on the bottom of the cartridge 2500. This boot in the bottom of the cartridge 2500 (e.g., full-perimeter boot that captures the outer perimeter of the plate 2650) may receive the upper face and inset sidewalls (shown in FIG. 26) on the top portion of the plate 2650 in interference fit to removably engage the cartridge 2500 with the plate 2650.

Figure 27:
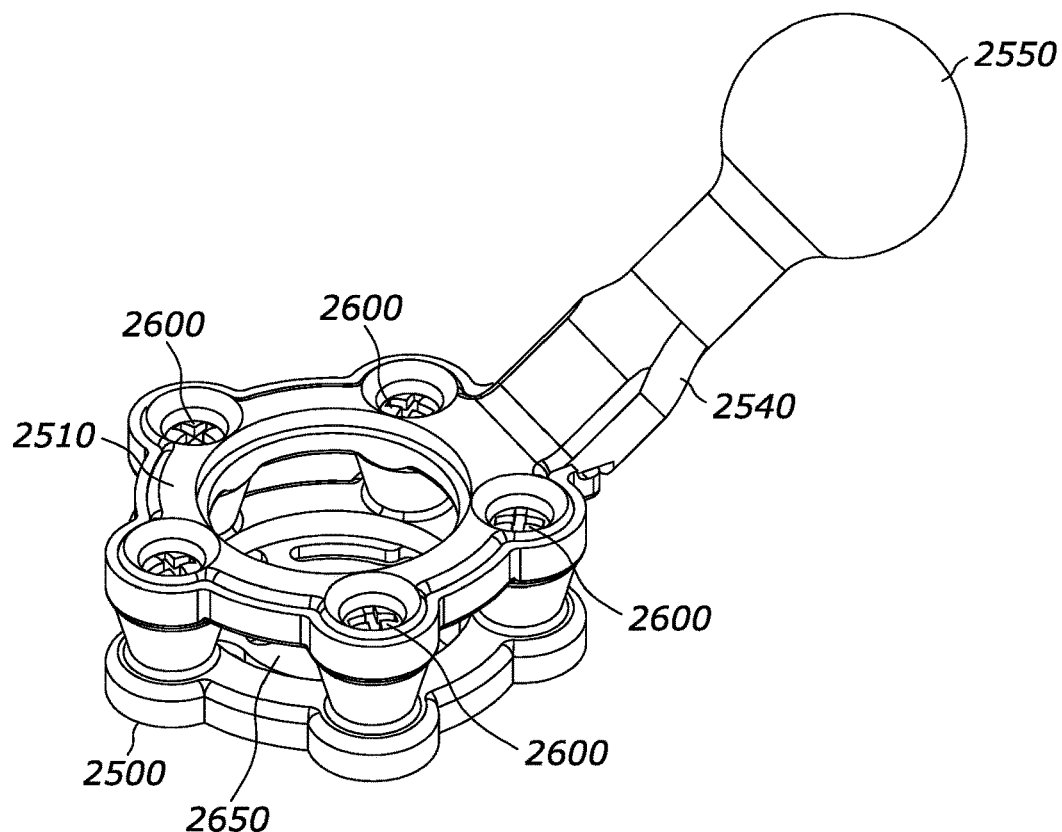
Figure 28:
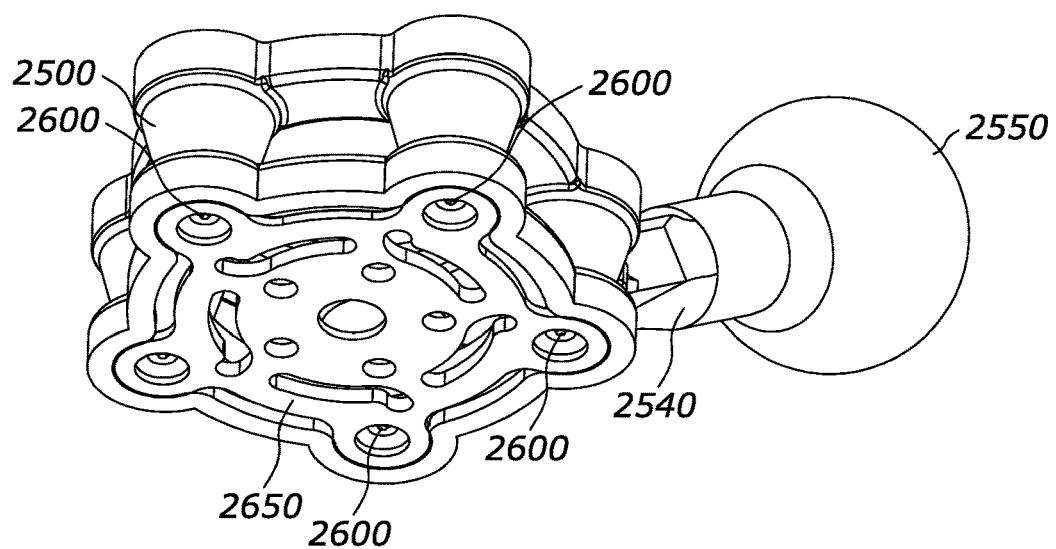
FIG. 28 shows a bottom isometric view of the third example embodiment as assembled together with a surgical plate consistent with present principles.

FIGS. 27 and 28 then show the combined plate/caddy assembly coupled together as a device head to then use with a device handle for fracture reduction. FIG. 27 shows the combined assembly in top isometric view, while FIG. 28 shows the combined assembly in bottom isometric view.

Figure 29:
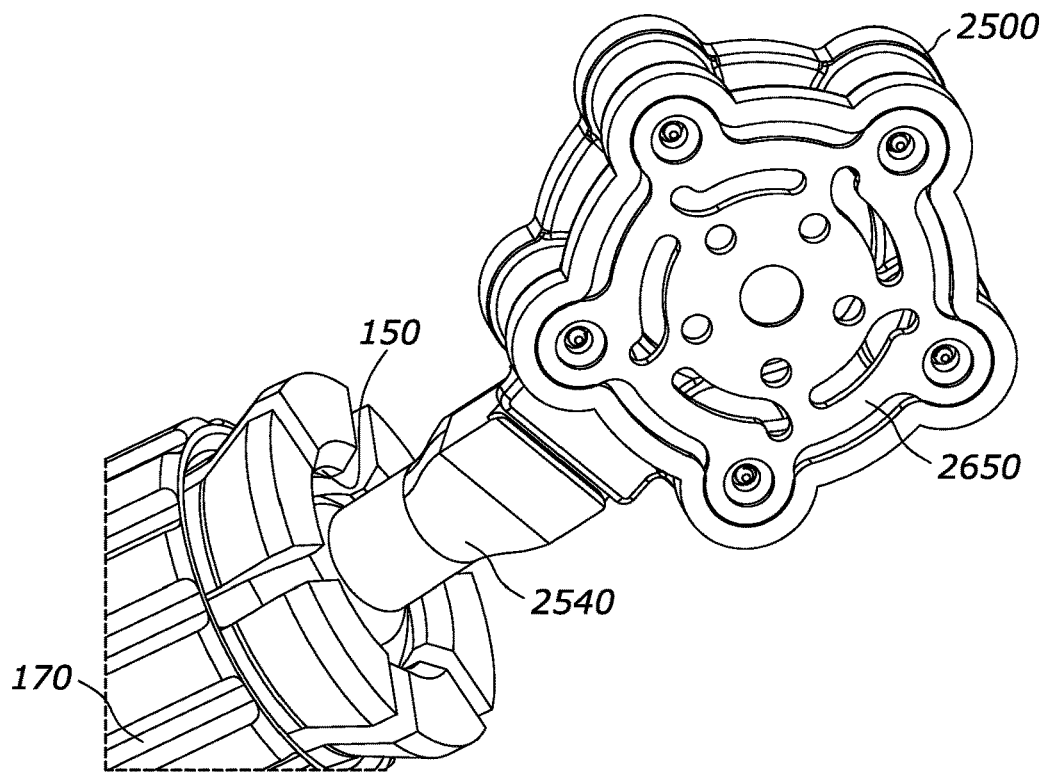
FIG. 29 shows a bottom isometric partial view of the third example embodiment as engaged with a handle of the device consistent with present principles.
Figure 30:
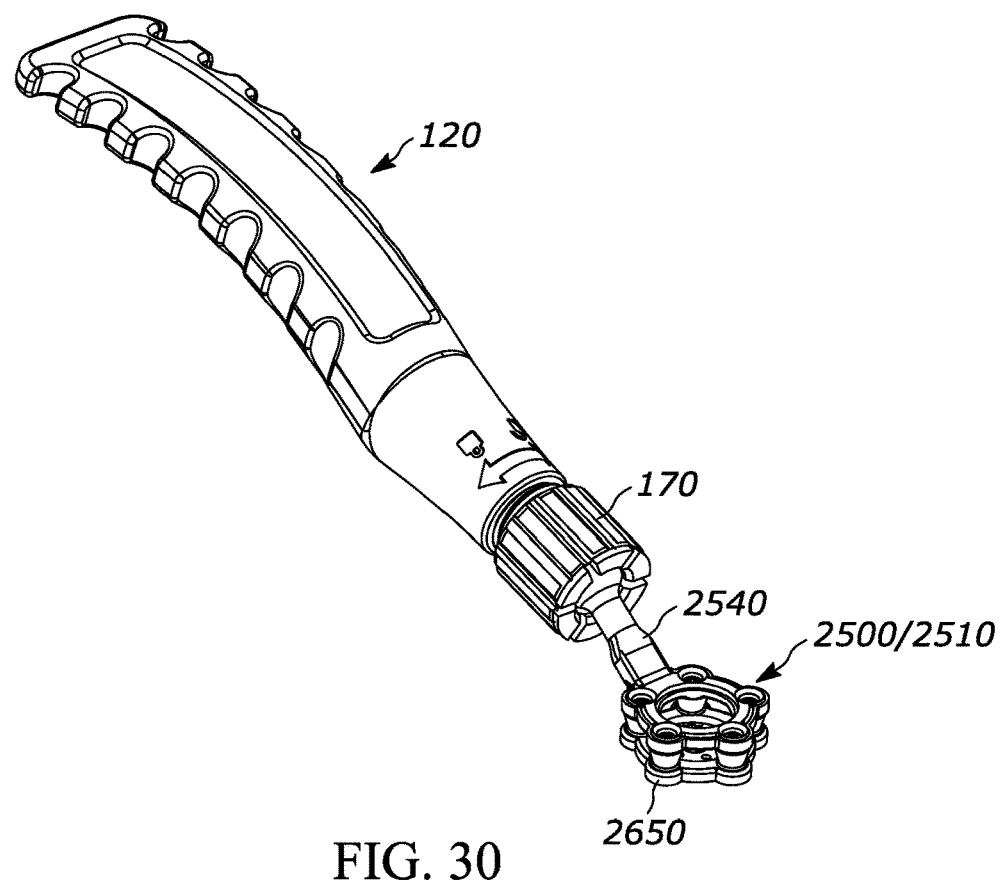
FIG. 30 shows an upper isometric view of the third example embodiment as engaged with a handle of the device consistent with present principles.

FIGS. 29 and 30 show the combined plate/caddy assembly of FIGS. 27 and 28 as engaged with a handle 120 via socket 150 that is locked into locked configuration via the collet 170 as described above. FIG. 29 is a bottom isometric partial view, while FIG. 29 is an isometric view. It may be appreciated from these figures that an all-in-one plate and screw delivery device is provisioned. It may also be appreciated that the geometry of the assembly 2500/2510 allows adequate surgeon visibility to the plate and wound surface and plate 2650.

Figure 31:
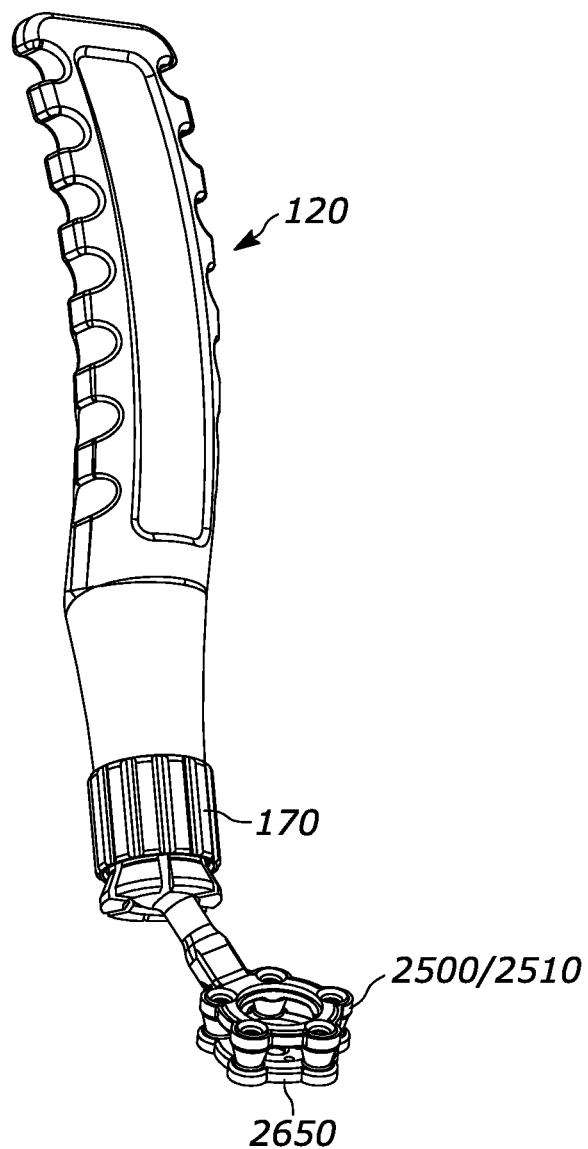
FIGS. 31 and 32 show isometric views of the third example embodiment in polyaxial articulation consistent with present principles.
Figure 32:
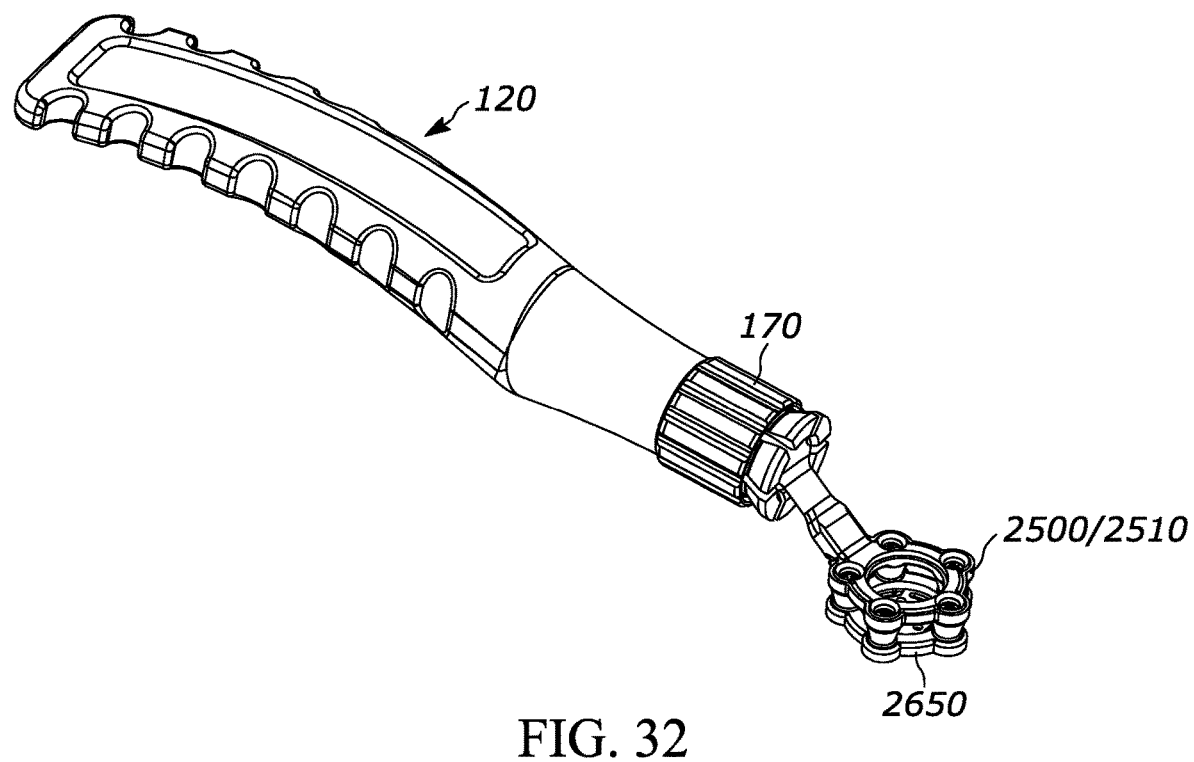

FIGS. 31 and 32 then show the same assembled medical device in polyaxial articulation via isometric views.

Figure 33:
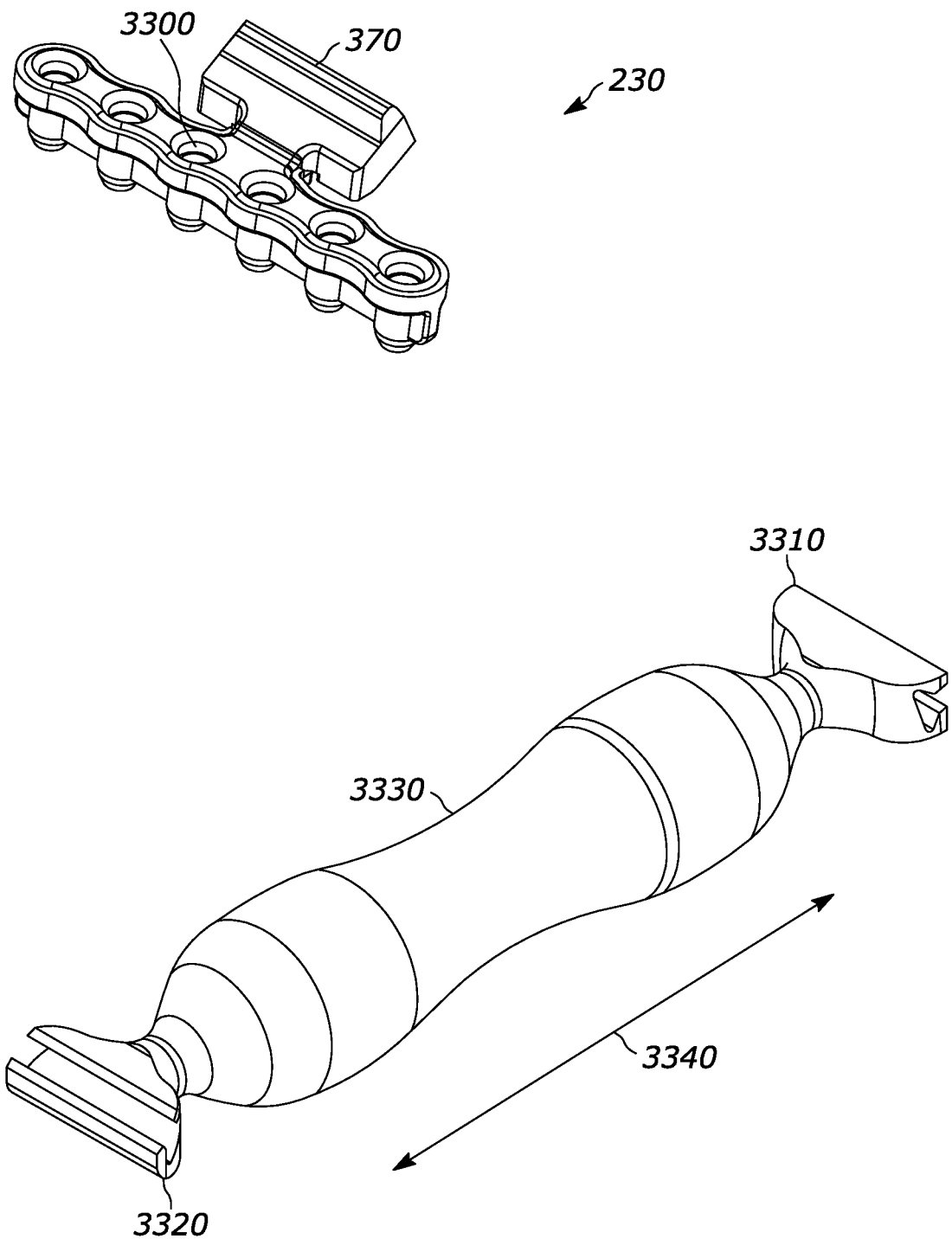
FIG. 33 shows an isometric view of a cartridge assembly and handle according to a fourth example embodiment of a medical device consistent with present principles.

Now in reference to FIG. 33, another example embodiment is shown. Here, the assembly 230 described above has been manufactured together and loaded with a screw 3300. The assembly 230 may then be transversely slid onto either holder 3310, 3320 at opposing ends of an hourglass-shaped handle 3300. The holders 3310, 3320 may be shaped to closely receive the contours of the rigid dovetailed male element 370 in friction fit similar to other embodiments described above. Also note that the holders 3310, 3320 may be inverted 180 degrees relative to each other about a longitudinal axis 3340 defined by the handle 3330, but with both holders 3310, 3320 still having openings facing outward.

Figure 34:
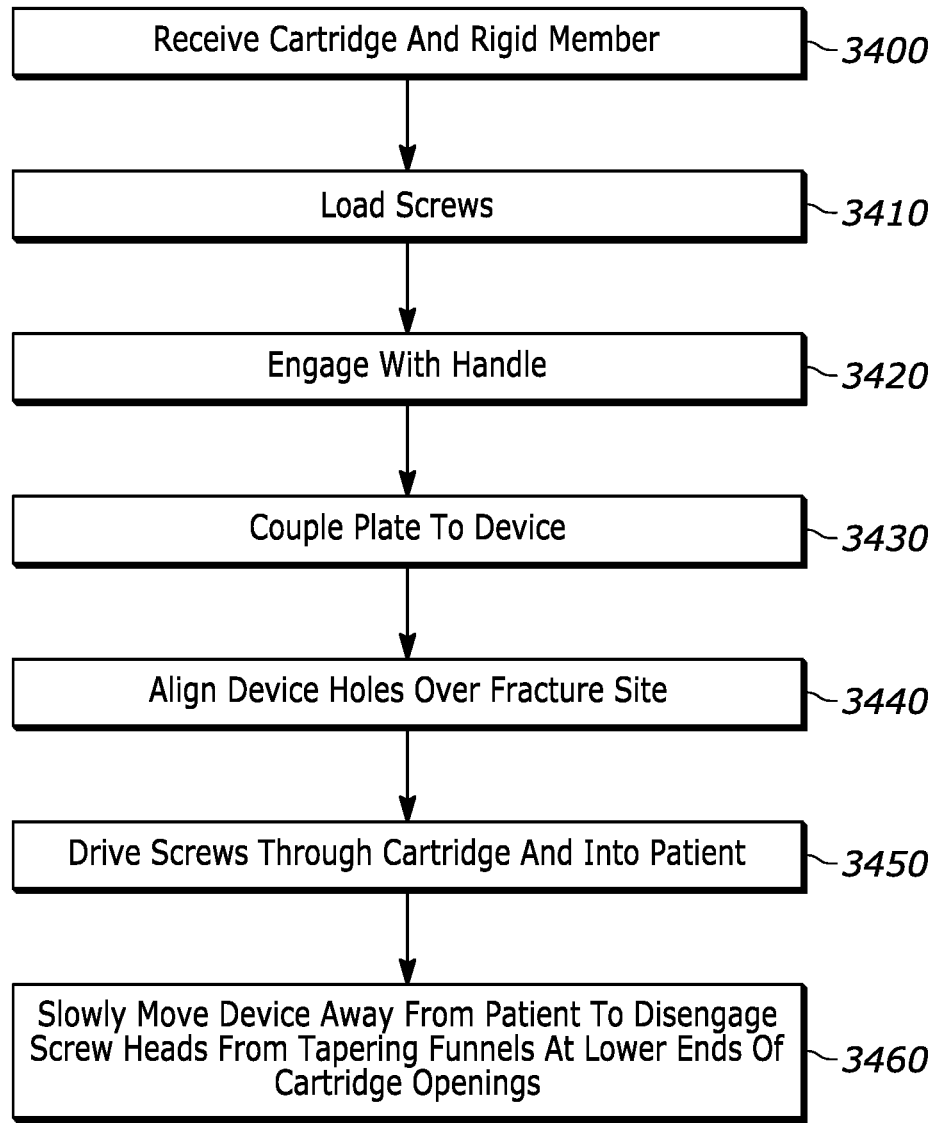
FIG. 34 shows an example method in flow chart format for surgically using a medical device consistent with present principles.

Continuing the detailed description in reference to FIG. 34, an example method/process flow for surgically using a medical device consistent with present principles is shown in flow chart format. Beginning at block 3400, the surgical process may begin with a medical professional receiving a non-rigid cartridge (e.g., the cartridge 300) already coupled to a rigid member (e.g., the member 350) from manufacture. The process may then proceed to block 3410 where the medical professional may load or otherwise extend surgical screws of a desired size into the cartridge (e.g., using a screwdriver) and then engage the cartridge assembly with a device handle at block 3420. The process may then flow to block 3430 where the medical professional may couple a surgical plate that will be used for fracture reduction to the rest of the device (e.g., using a clamp or vice as described above)

Thereafter, the logic may proceed to block 3440 where the medical professional may align device holes and aligned plate holes over a fracture site as desired for fracture reduction. Then at block 3450 the medical professional may drive or otherwise extend the screws through the cartridge and into the patient, securing the plate to the patient for fracture reduction in the process. Thereafter, the process may move to step 3460 where the medical professional may slowly move the medical device away from the patient to disengage the screw heads from the tapering funnels at the lower ends of the cartridge openings.

Note that while some steps above have been described as being performed by a medical professional, in other instances certain steps may be performed by a manufacturer or other third party, such as a manufacturer that might pre-assemble the medical device 100 and pre-load it with screws or other fasteners. Also note that some of the steps of FIG. 34 may be performed in a different order than that described above (e.g., steps 3400-3430), and that certain steps may not be performed at all. For example, a medical device consistent with present principles may be loaded with screws and then the device may be used to engage the screws with a surgical plate for facture reduction without the surgical plate ever being removably engaged to the medical device itself.

Figure 35:
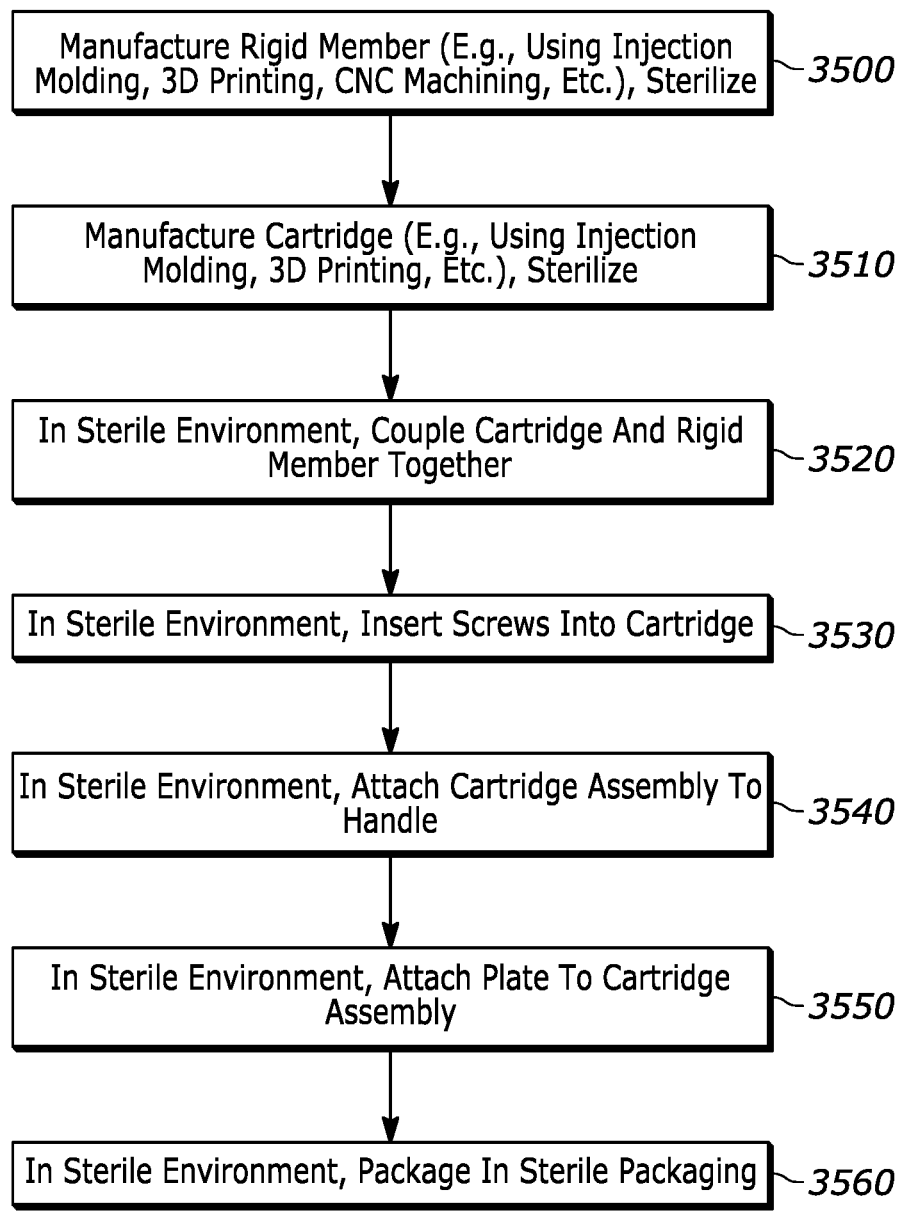
FIG. 35 shows an example method in flow chart format for manufacturing a medical device consistent with present principles.

Now in reference to FIG. 35, an example method/process flow for manufacturing a medical device consistent with present principles is shown in flow chart format. Beginning at block 3500, the manufacturing process may begin with a manufacturer manufacturing a rigid member consistent with present principles (e.g., a member 350), such as through injection molding, three-dimensional (3D) printing, computer numerical control (CNC) manufacturing, or other methods. Also at block 3500, the manufactured rigid member may be sterilized.

The process may then flow to block 3510 where the manufacturer may manufacture a non-rigid cartridge consistent with present principles (e.g., a cartridge 300). This might be done through injection molding, three-dimensional (3D) printing, or other methods. Also at block 3510, the manufactured cartridge may be sterilized. Sterilization of the cartridge (and other components) may involve use of ethylene oxide, gamma radiation, e-beam radiation, chlorine dioxide, etc., for example.

From block 3510 the process may then proceed to block 3520. At block 3520 and while still in a sterile environment, the manufacturer may couple the sterilized cartridge to the sterilized rigid member as a permanent assembly (e.g., if not done already via over-molding of the cartridge onto the rigid member during manufacture of the cartridge itself). For example, at block 3520 an adhesive may be used to couple the two components together. Then at block 3530 while still in the sterile environment, the manufacturer may insert sterilized screws into the cartridge (e.g., using a screwdriver) and then, at block 3540, attach the cartridge assembly (with screws) to a handle like the handle 120 in a manner as described above. The process may then flow to block 3550 where, still in the sterile environment, the manufacturer may attach a surgical plate to the cartridge assembly and then, at block 3560, package the entire assembly together in sterile packaging for shipment.

Note that while some steps above have been described as being performed by a manufacturer, in other instances certain steps may be performed by a medical professional or other third party, such as a medical professional loading the cartridge with screws or loading the cartridge assembly onto the handle. Also note that the steps of FIG. 35 may be performed in a different order than that described above, and that certain steps may not be performed at all.

Figure 36:
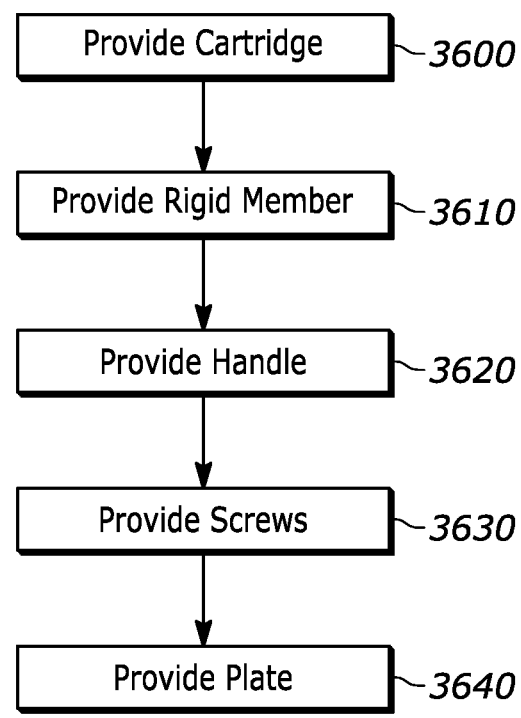
FIG. 36 shows an example method in flow chart for providing a medical device consistent with present principles.
Figure 37A:
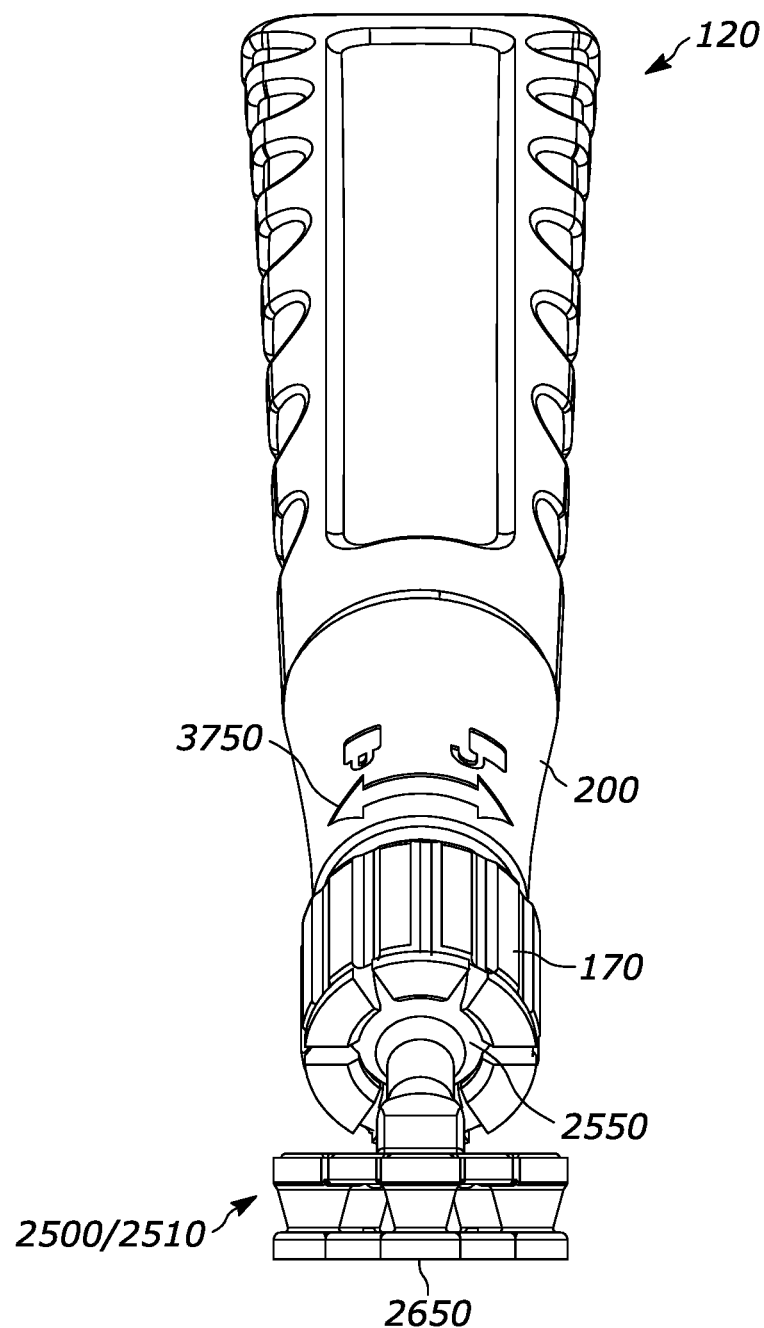
FIGS. 37A-37E show respective front, top, right side, cross section right, and isometric views of an example burr-shape embodiment consistent with present principles.
Figure 37B:
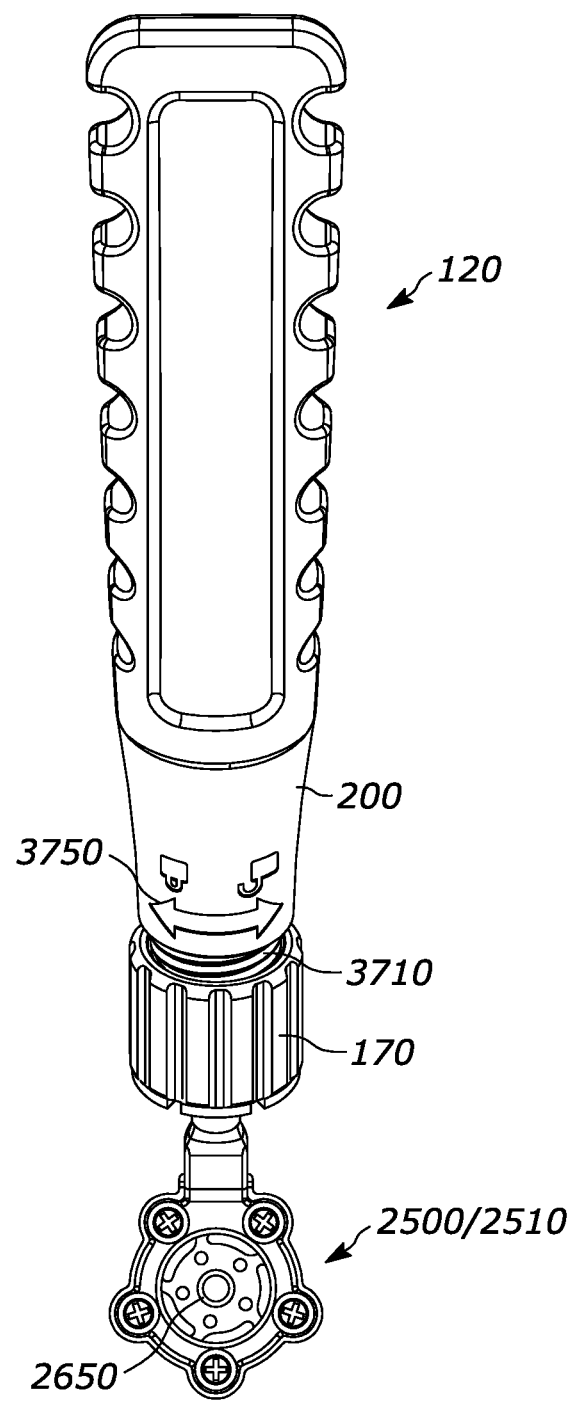
Figure 37C:
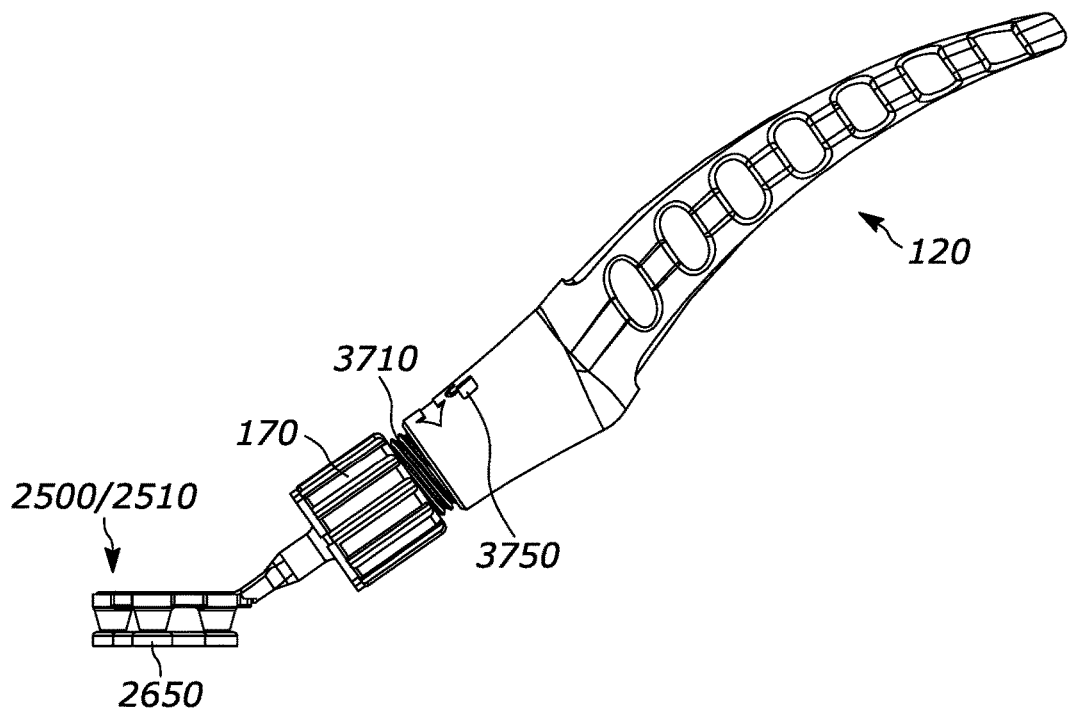
Figure 37D:
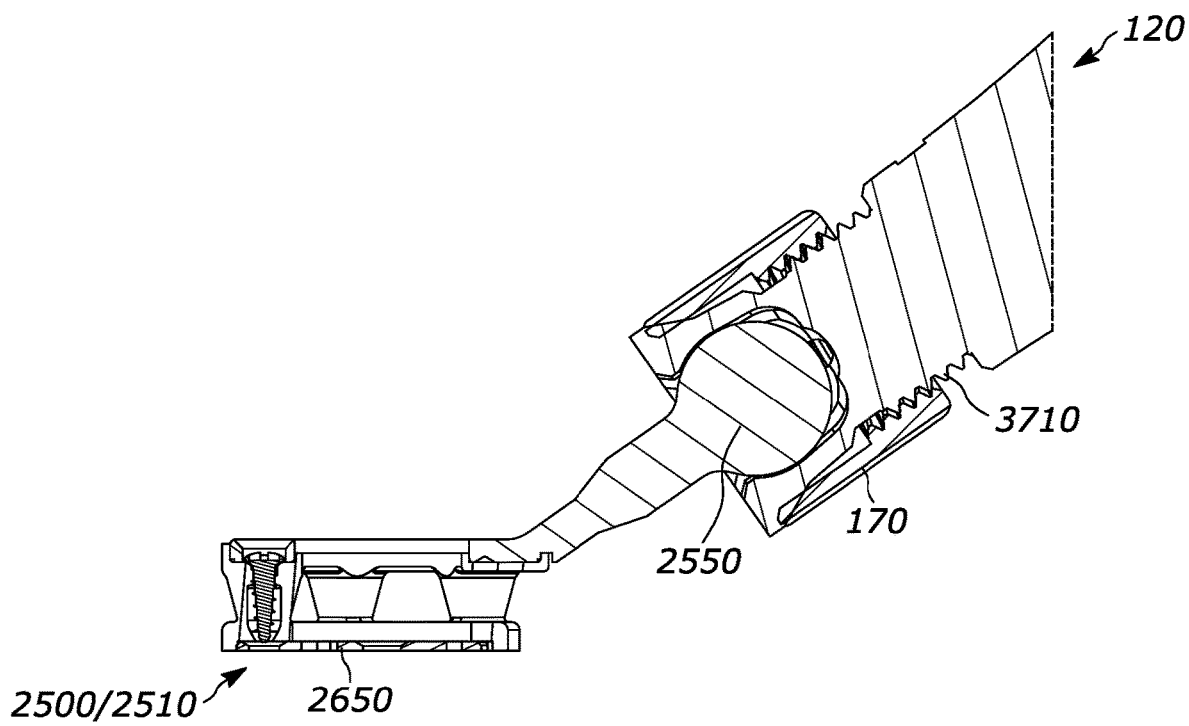
Figure 37E:
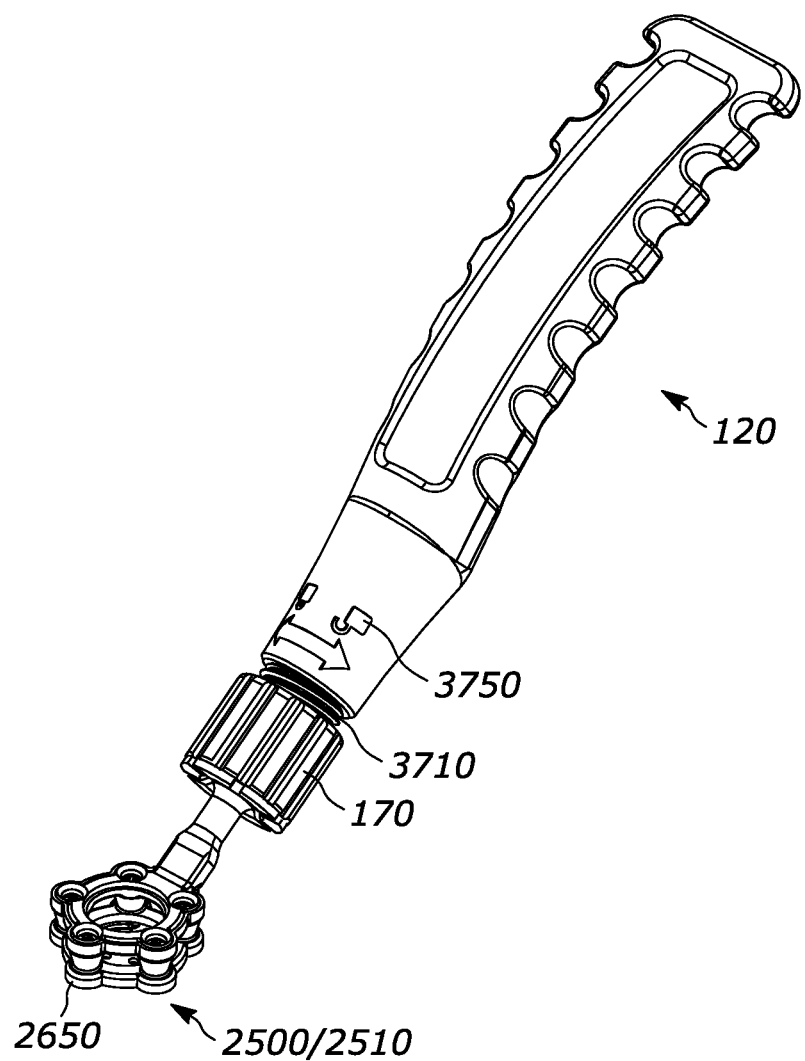

Turning now to FIG. 36, yet another example process flow is shown. The process flow of FIG. 36 may be used for vending or otherwise providing a medical device consistent with present principles through the channels of commerce to a medical professional.

FIG. 36 is also shown in flow chart format and, beginning at block 3600, the process may start with the provider providing a cartridge like the cartridge 300 consistent with present principles. Then at step 3610 the provider may provide a rigid member like the member 350 consistent with present principles, again noting that in certain examples the cartridge and rigid member may be coupled/bonded together at manufacture prior to being provided. Thereafter, at step 3620 the provider may provide a handle like the handle 120 consistent with present principles. Then at step 3630 the provider may provide screws and, at step 3640, a surgical plate.

Note that while some steps above have been described as being performed by a provider, in other instances certain steps may be performed by a manufacturer or other third party. Also note that the steps of FIG. 36 may be performed in a different order than that described above, and that certain steps may not be performed at all.

Now in reference to FIGS. 37A-37E, these figures show respective front, top, right side, cross section right, and isometric views of an example device consistent with present principles. The device may include the handle 120 as well as a CMF burr hole cartridge assembly 2500/2510. Among other things, these figures demonstrate that the collar 200 on the handle 120 may include markings 3750 indicating a first direction in which the collet 170 may be twisted to lock the ball 2550 within the socket (the direction of the locked graphical lock shown) and indicating an opposite direction in which the collet 170 may be twisted to unlock the ball 2550 from the socket (the direction of the unlocked graphical lock shown). Note that female threads 3710 onto which the male threads inside the collet 170 may screw are also shown.

Figure 38A:
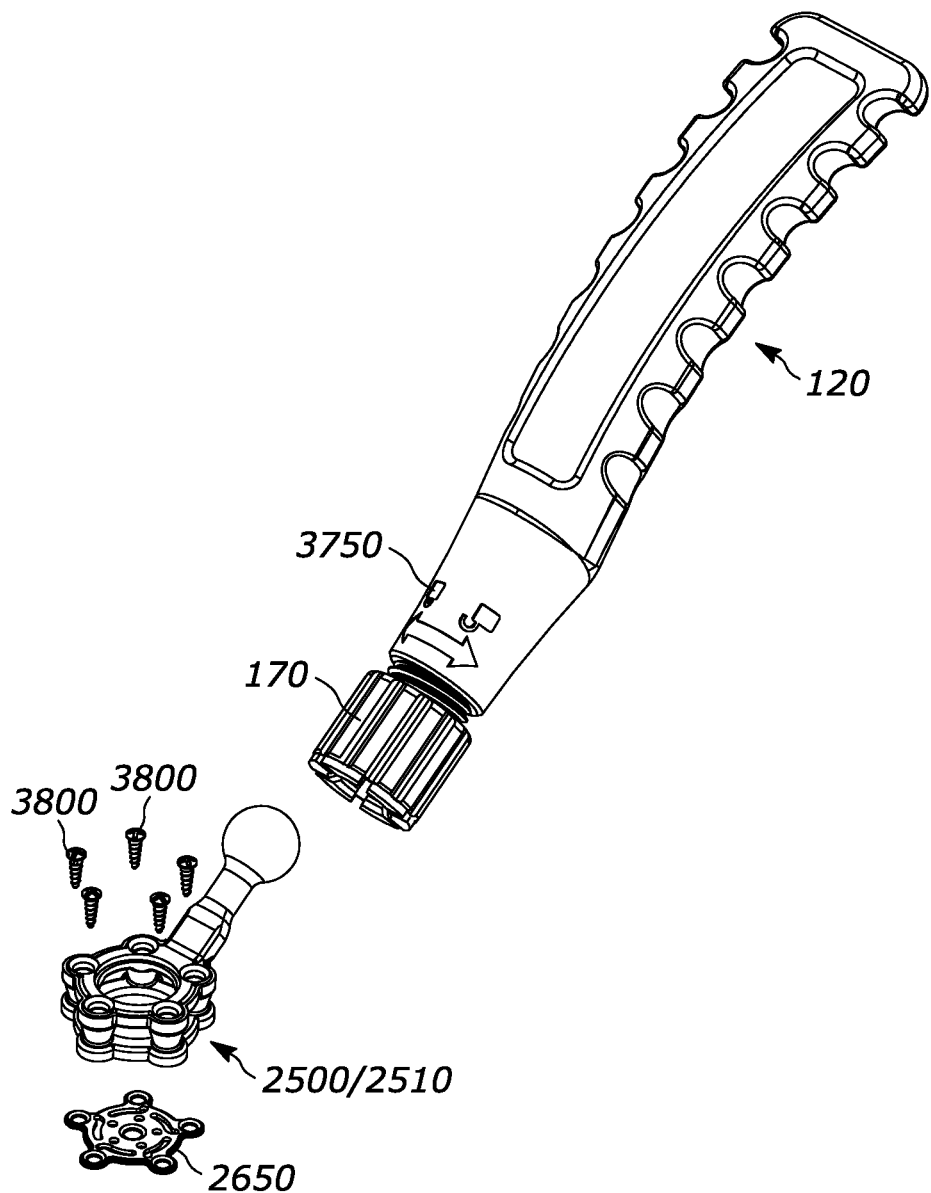
FIGS. 38A, 38B, and 38C show respective exploded isometric, exploded side, and exploded isometric views of the same setup as FIGS. 37A-37E.
Figure 38B:
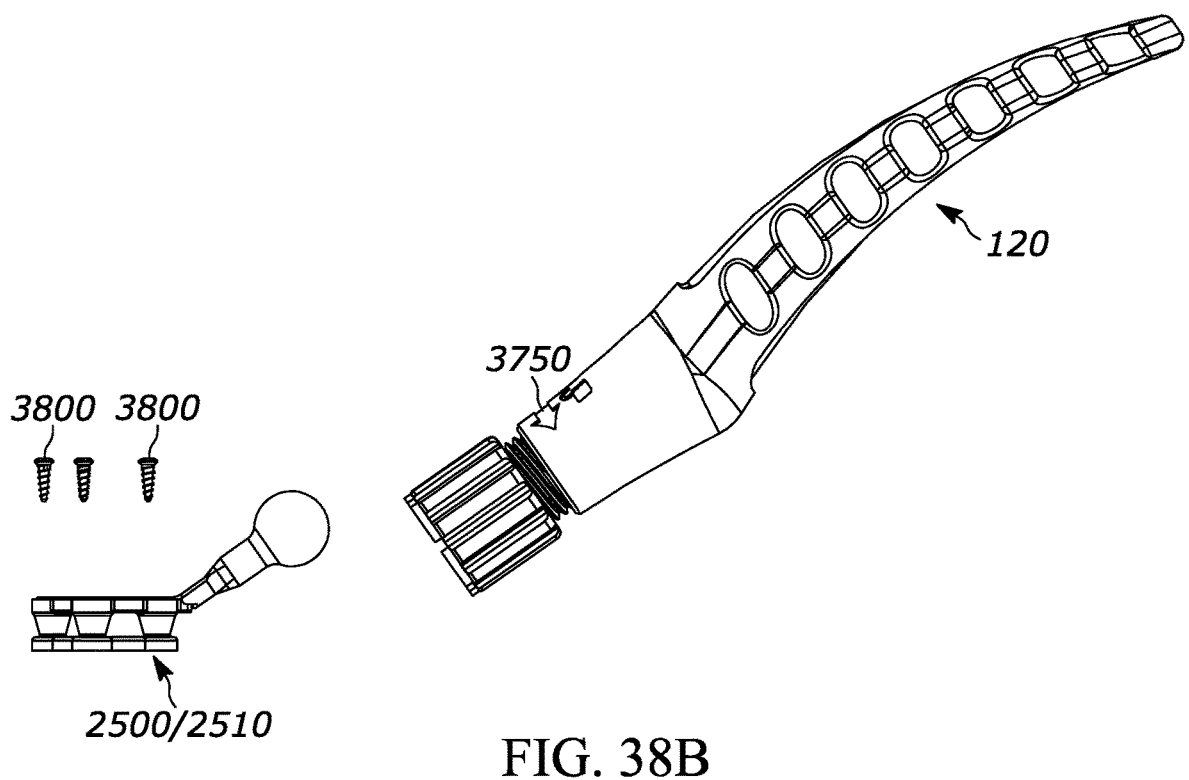
Figure 38C:
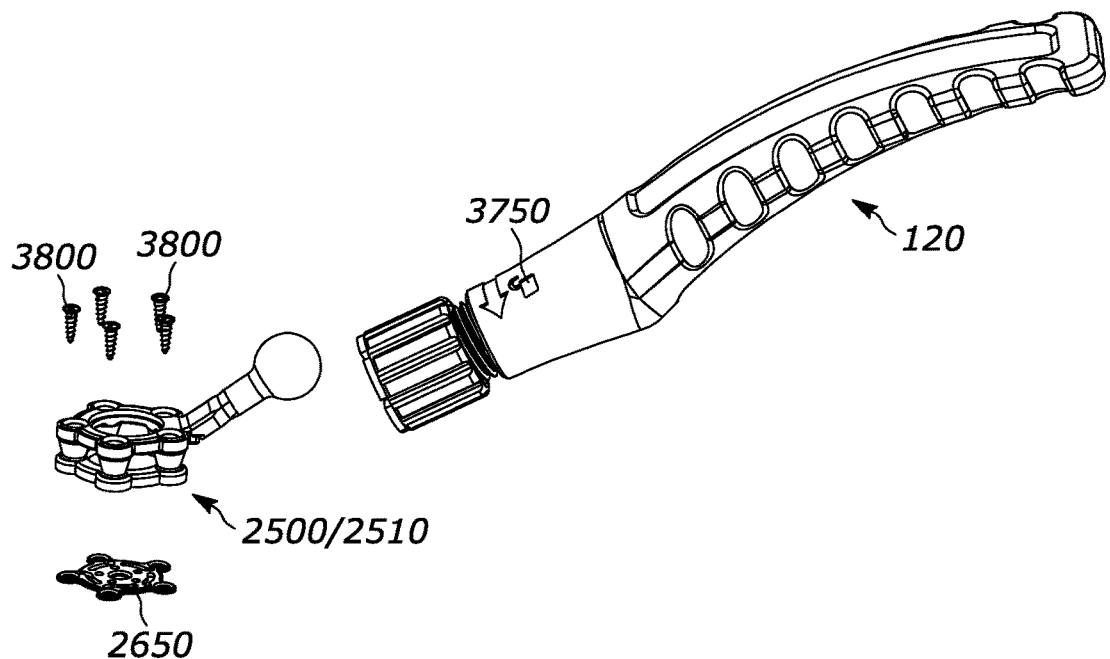

FIG. 38A then shows an exploded isometric view of screws 3800 prior to being inserted into the assembly 2500/2510 and showing a boot-style plate holder similar to as described above in reference to FIG. 26. FIG. 38B shows an exploded side view, and 38C another exploded isometric view, of the same setup.

Figure 39A:
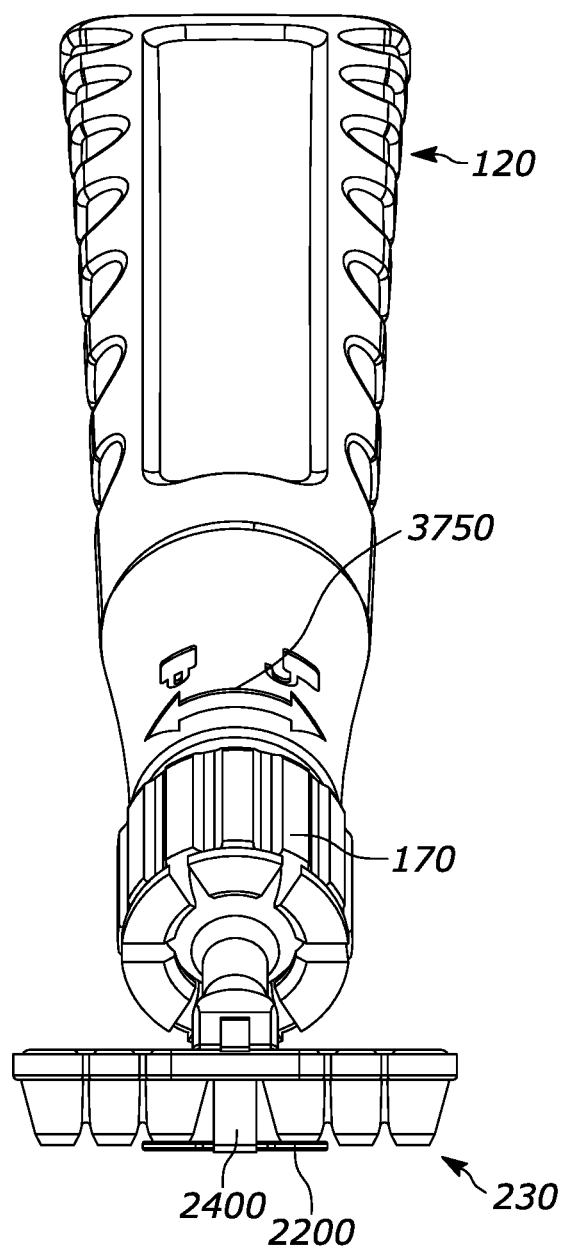
Figure 39B:
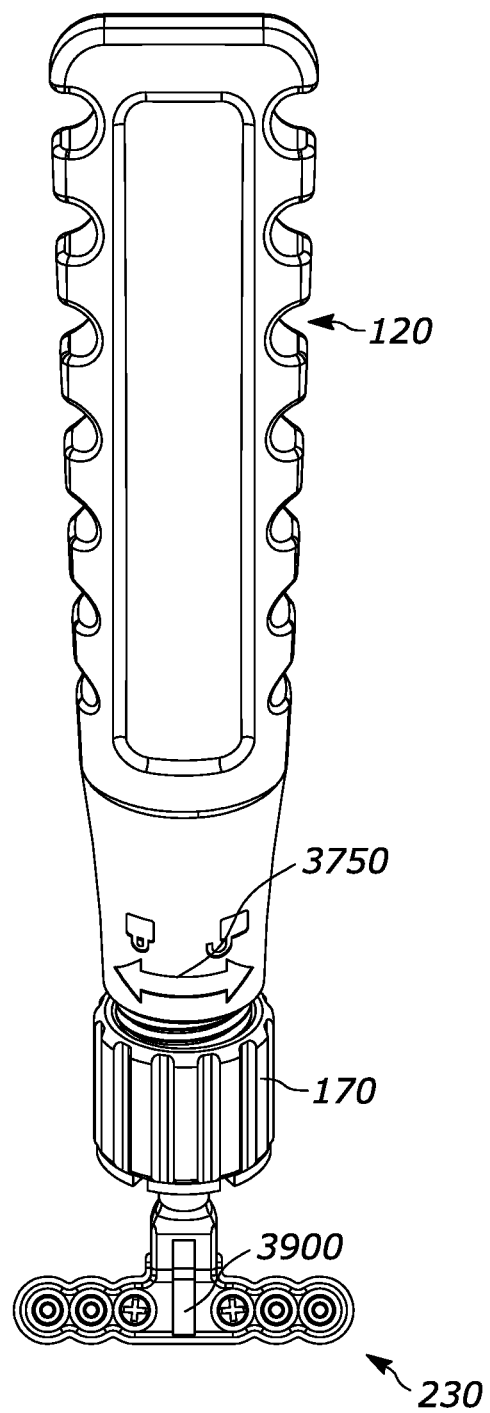
Figure 39C:
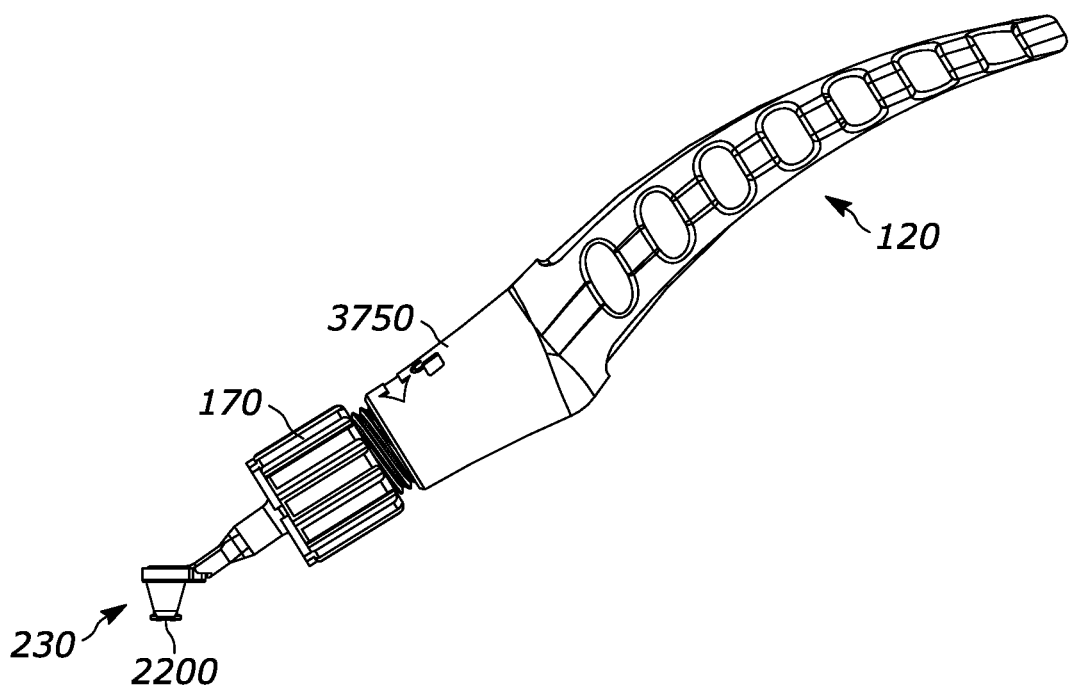
Figure 39D:
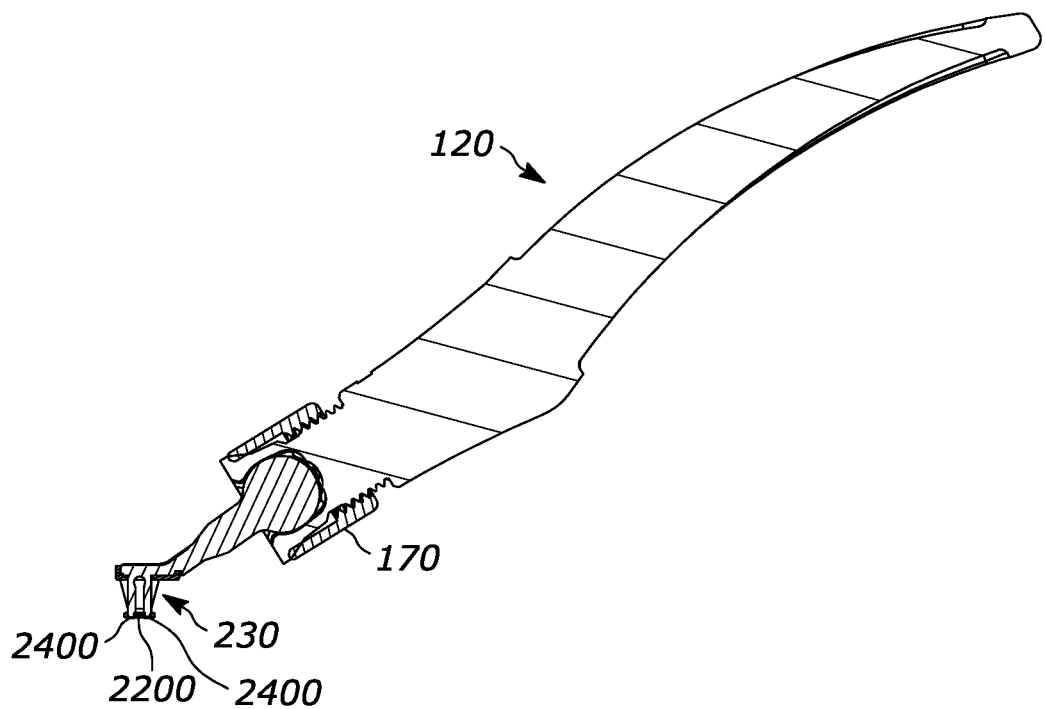
Figure 39E:
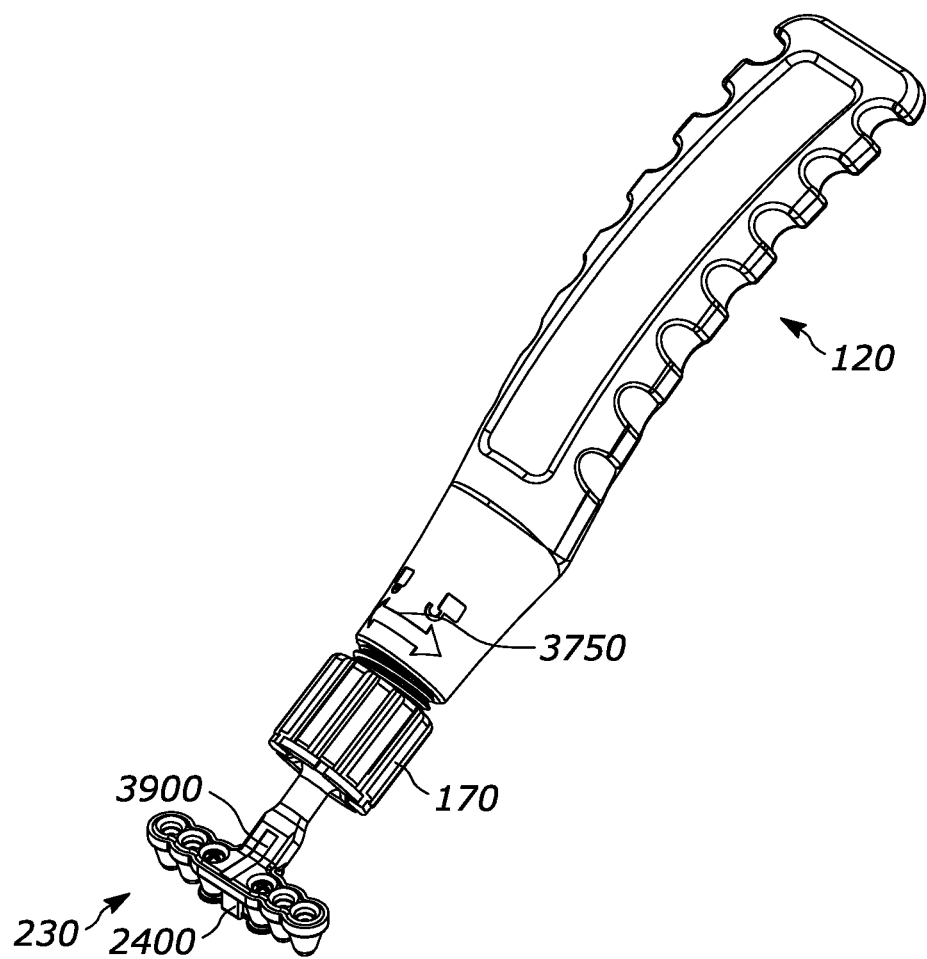

FIGS. 39A-39E show respective front, top, right side, cross section right, and isometric views of the example device 100 according to the first example embodiment above consistent with present principles. As such, the assembly 230 is coupled to the handle 120, and the markings 3750 are also included here. As shown in FIGS. 39B and 39E in particular, a measurement or marking 3900 may be included in the middle of the rigid member 350 to help the surgeon align the assembly 230 and H-plate 2200 as desired over a fracture site (e.g., bone plate alignment across fracture line). Other measurements and markings may also be included on other portions of the cartridge and rigid member, if desired.

In certain specific examples, each measurement or marking may be established by laser-marking.

Figure 40A:
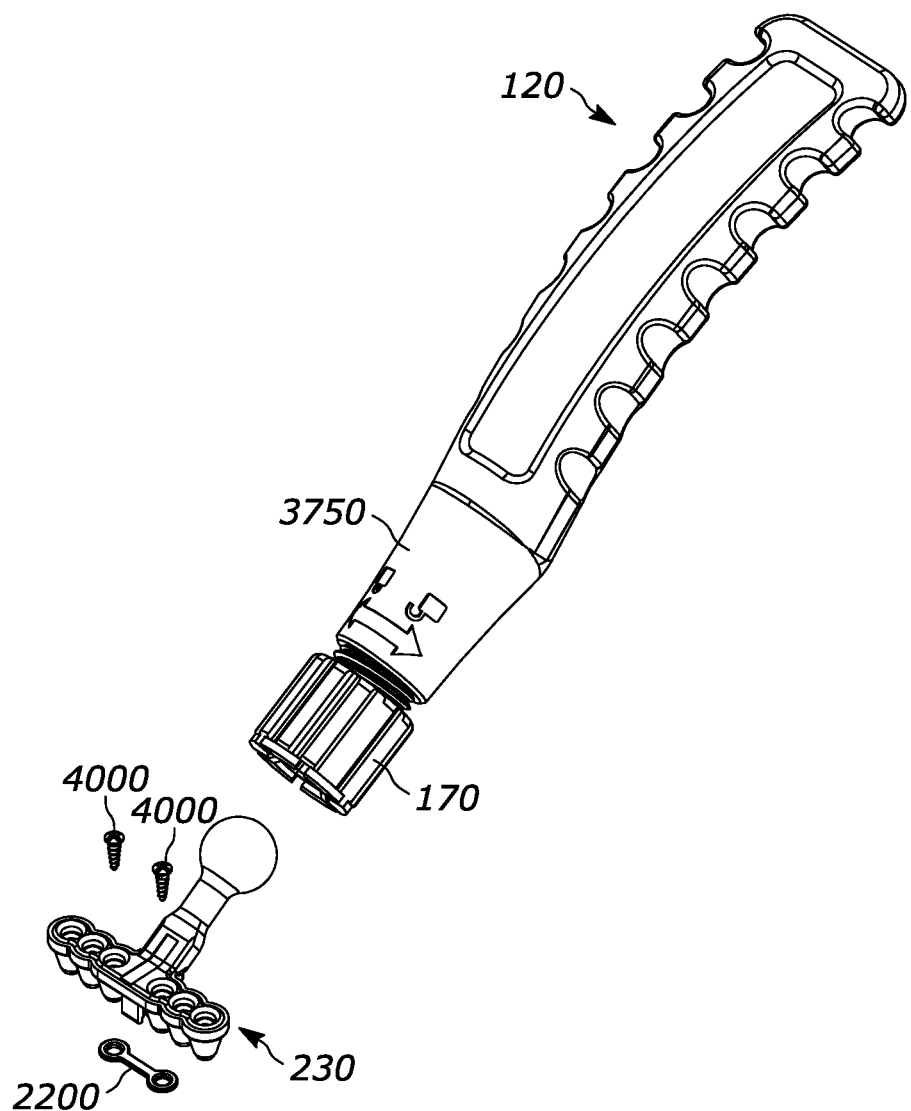
FIGS. 40A, 40B, 40C, and 40D show respective exploded isometric, exploded side, exploded isometric, and exploded cross-sectional views of the same setup as FIGS. 39A-39E.
Figure 40B:
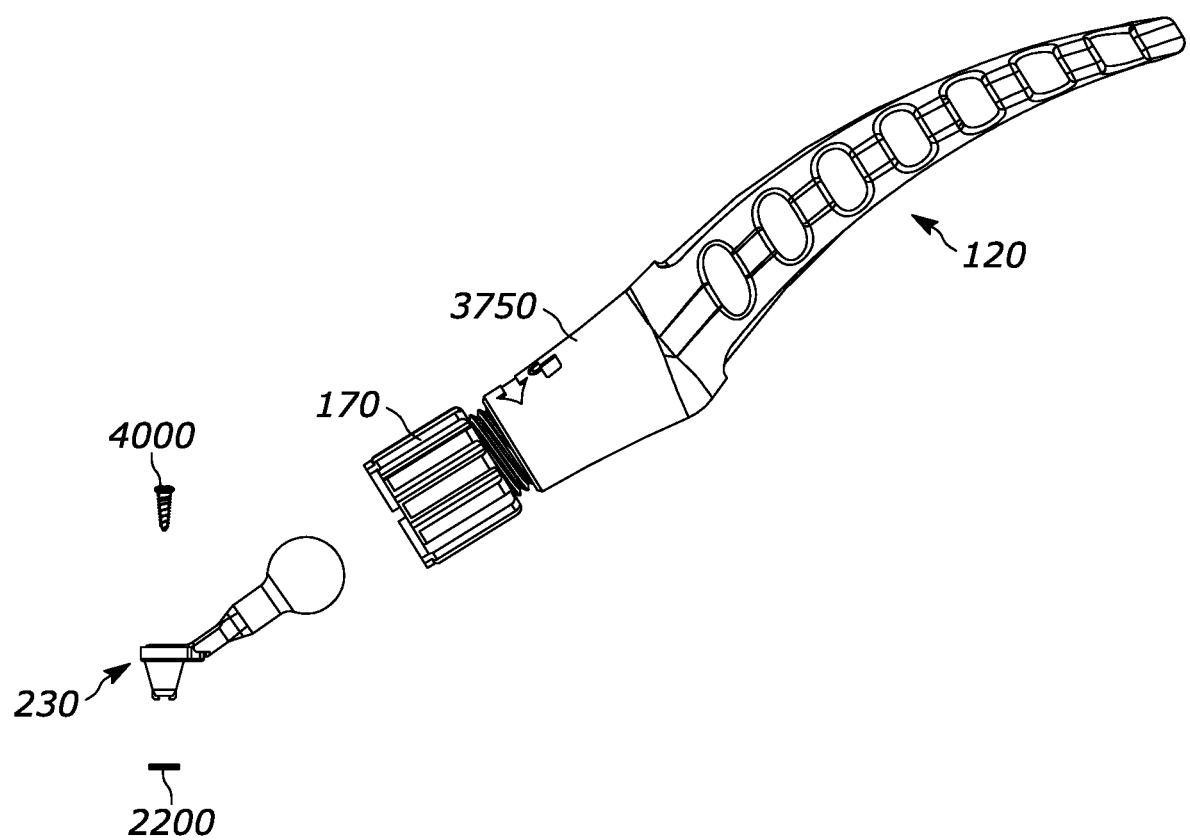
Figure 40C:
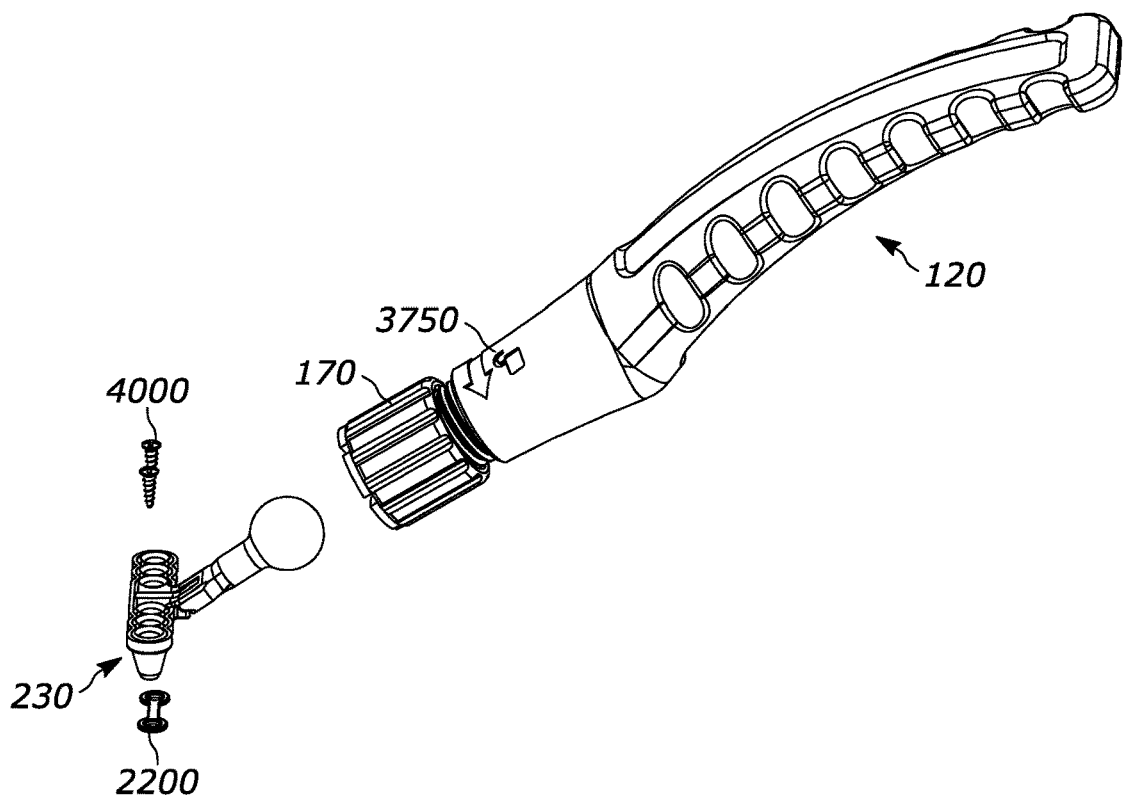
Figure 40D:
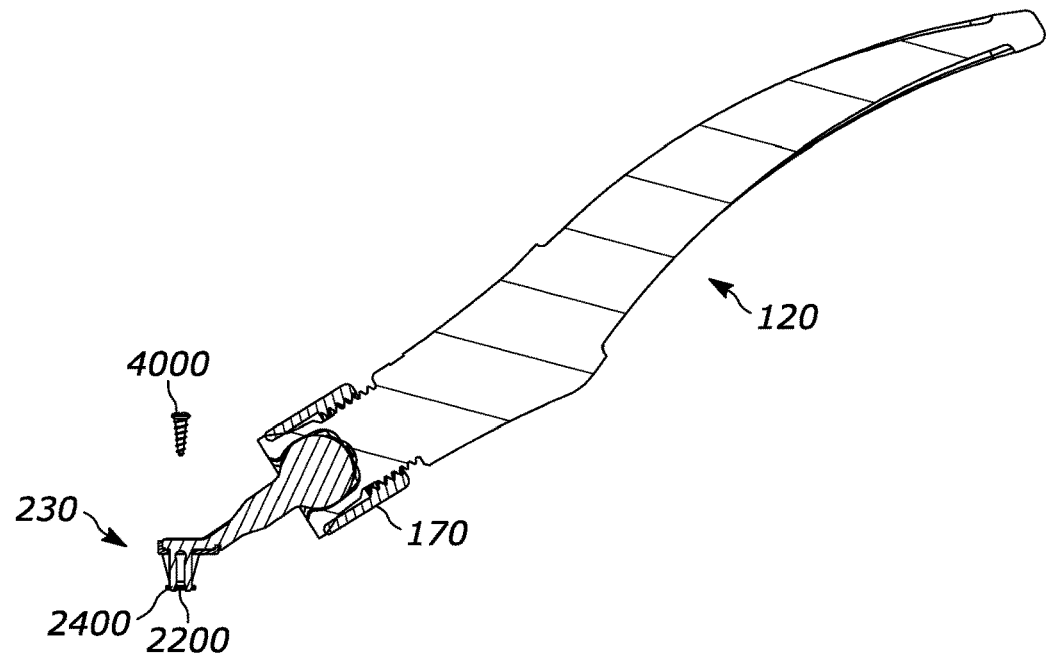
Figure 41A:
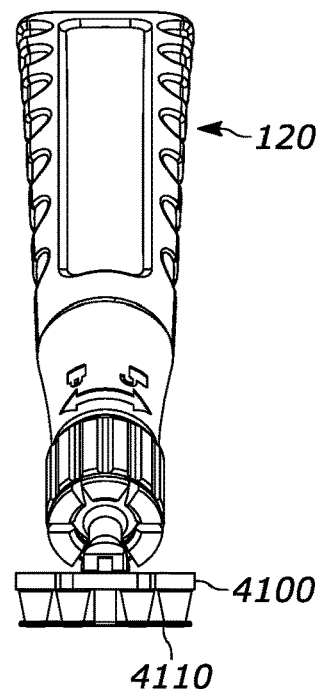
FIGS. 41A-41E show respective front, top, right side, cross section right, and isometric views of an example dog-bone shape embodiment consistent with present principles.
Figure 41B:
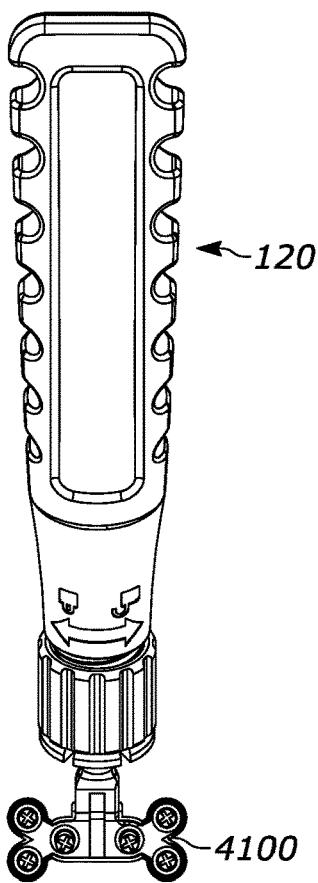
Figure 41C:
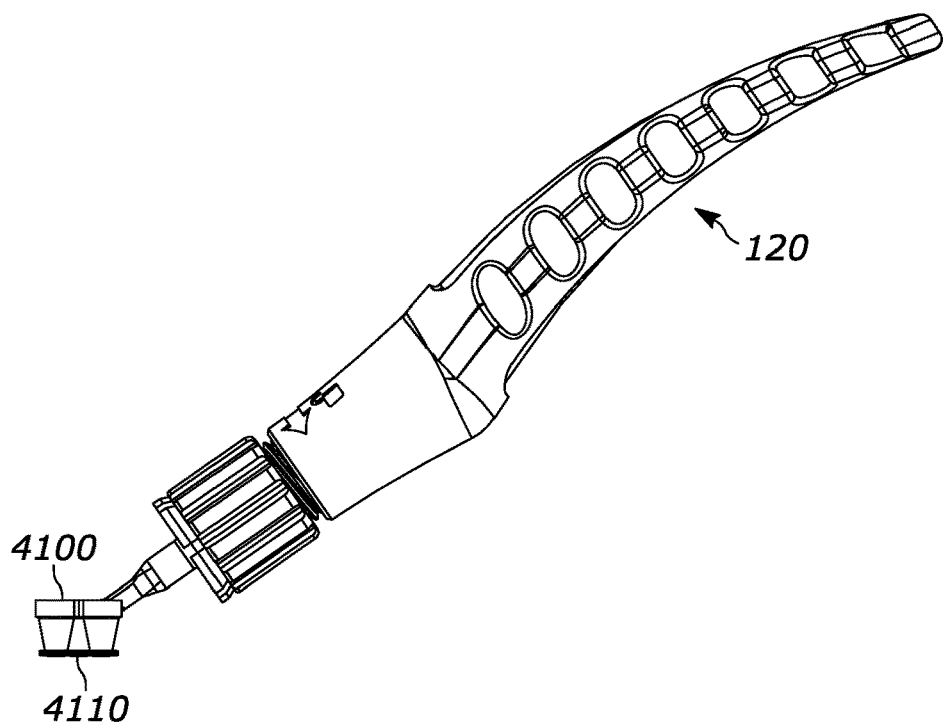
Figure 41D:
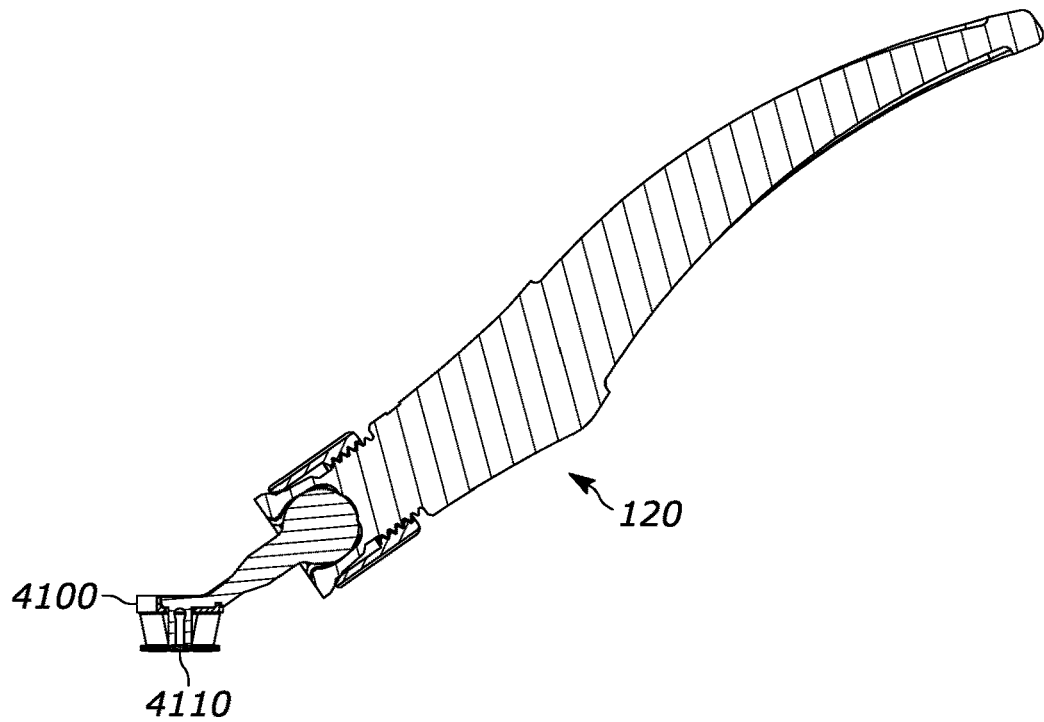
Figure 41E:
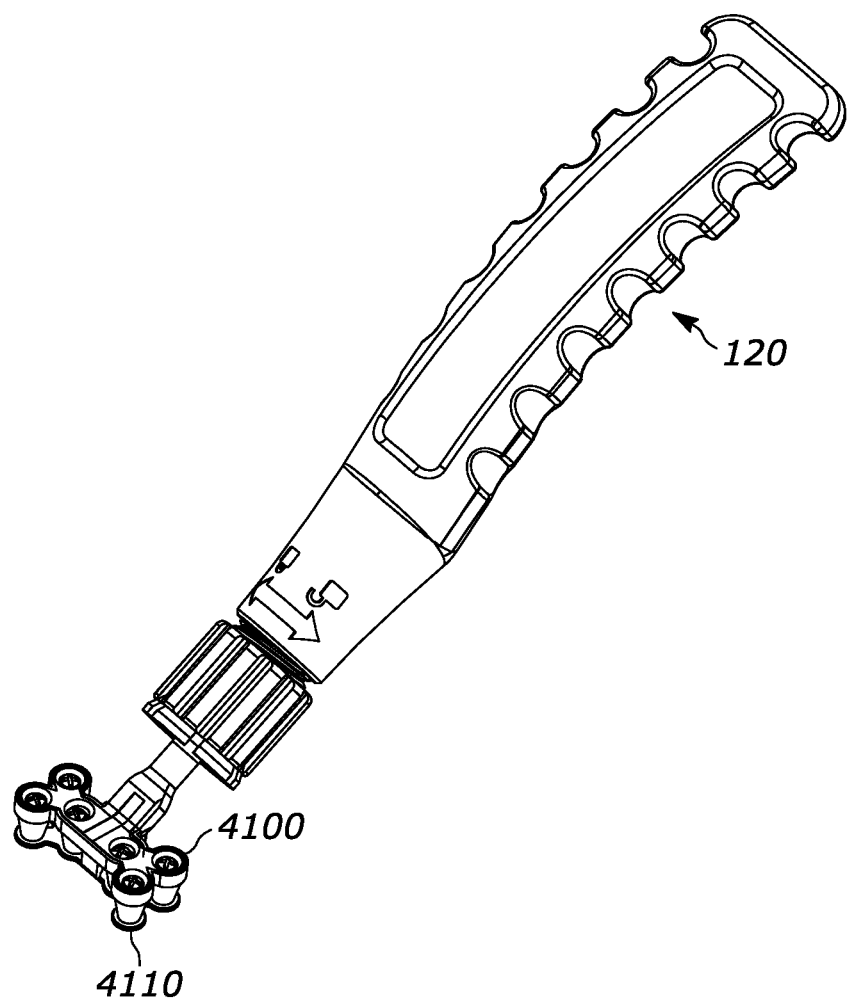

FIG. 40A then shows an exploded isometric view of the device 100 with screws 4000 prior to being inserted into the assembly 230, and shows the element(s) 2400 as described above to attach the plate 2200 to the cartridge 300 as also described above. FIG. 40B shows an exploded side view, and 40C another exploded isometric view, of the same setup. FIG. 40D shows an exploded cross-sectional view of the same setup.

Figure 42A:
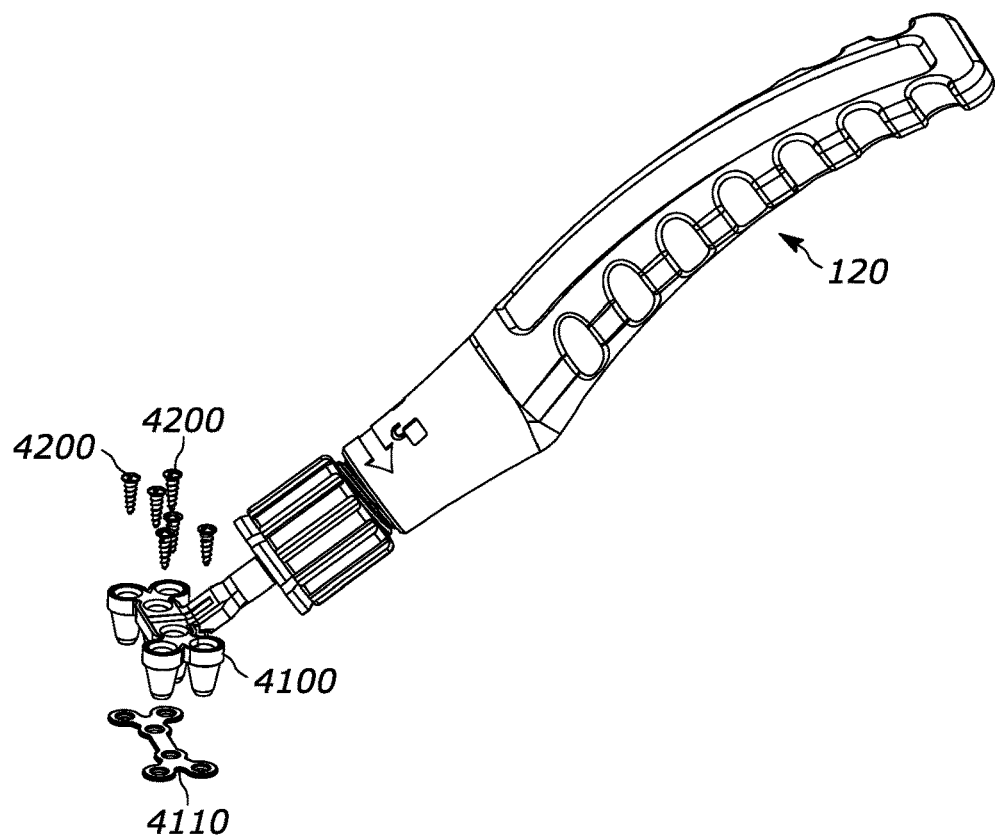
FIGS. 42A, 42B, and 42C show respective exploded isometric, exploded side, and exploded isometric views of the same setup as FIGS. 41A-41E.
Figure 42B:
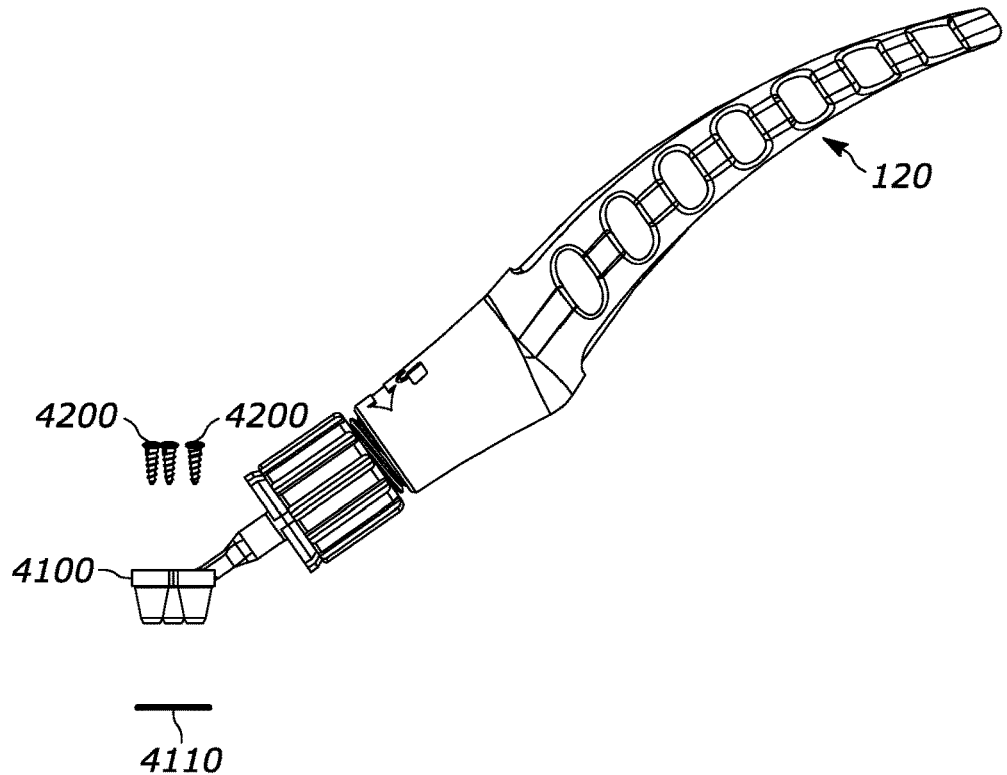
Figure 42C:
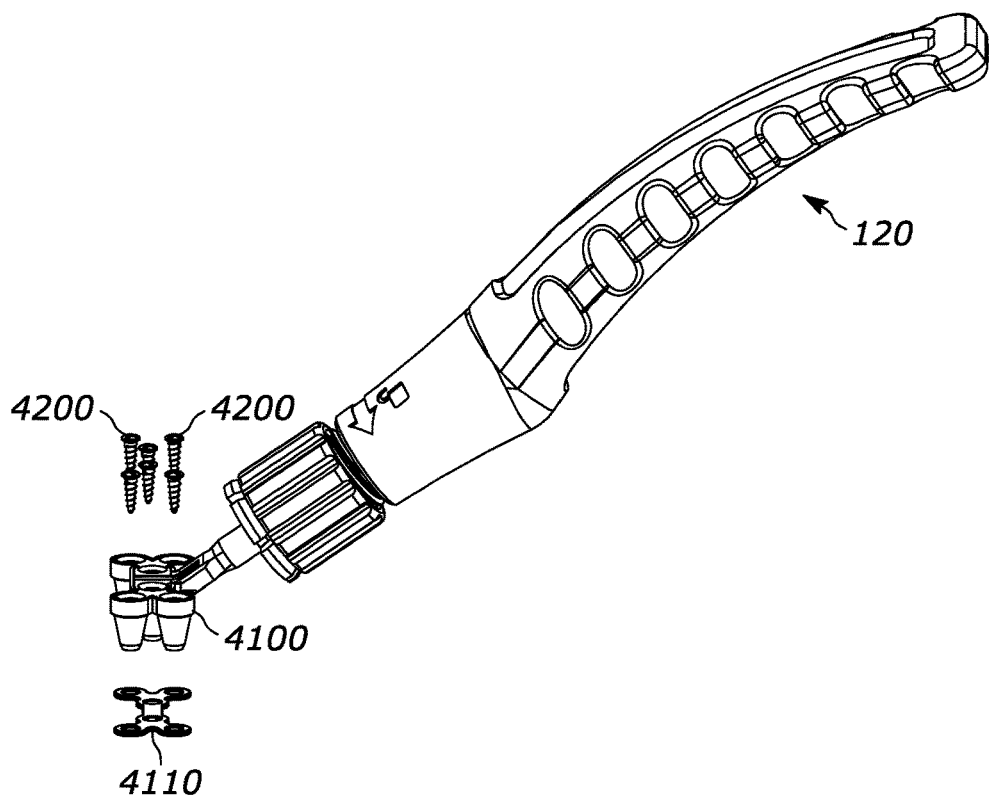
Figure 43A:
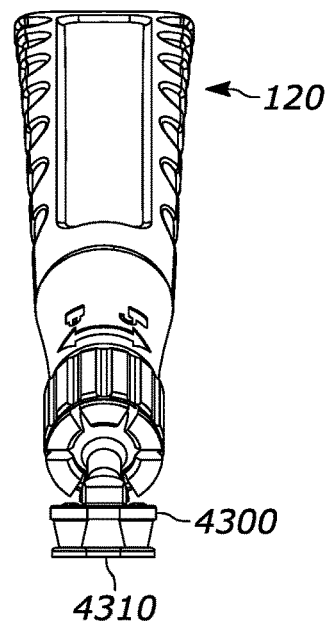
FIGS. 43A-43E show respective front, top, right side, cross section right, and isometric views of an example square-shape embodiment consistent with present principles.
Figure 43B:
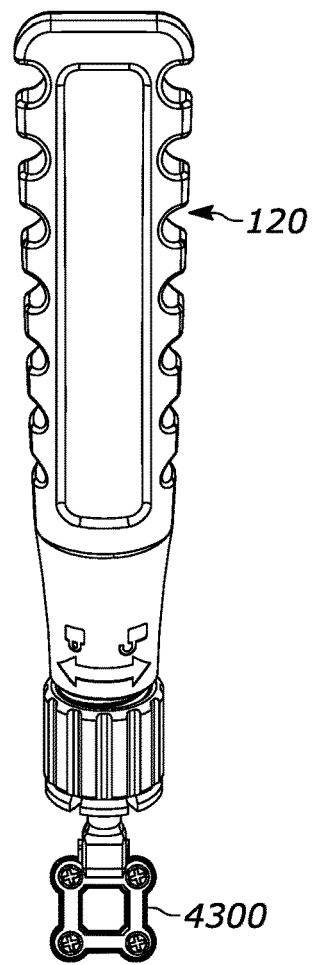
Figure 43C:
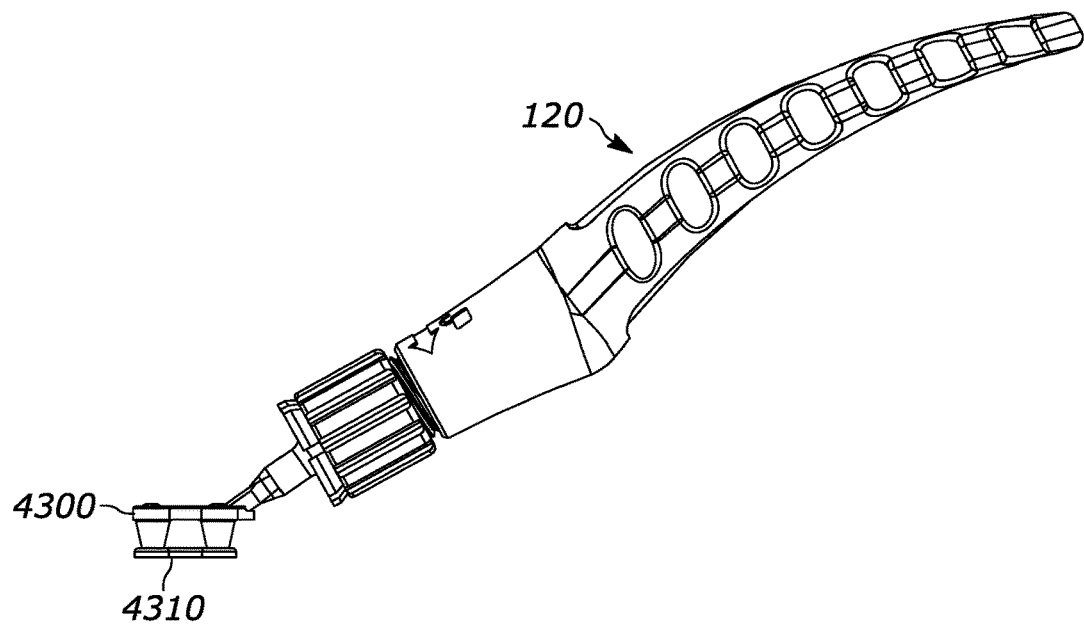
Figure 43D:
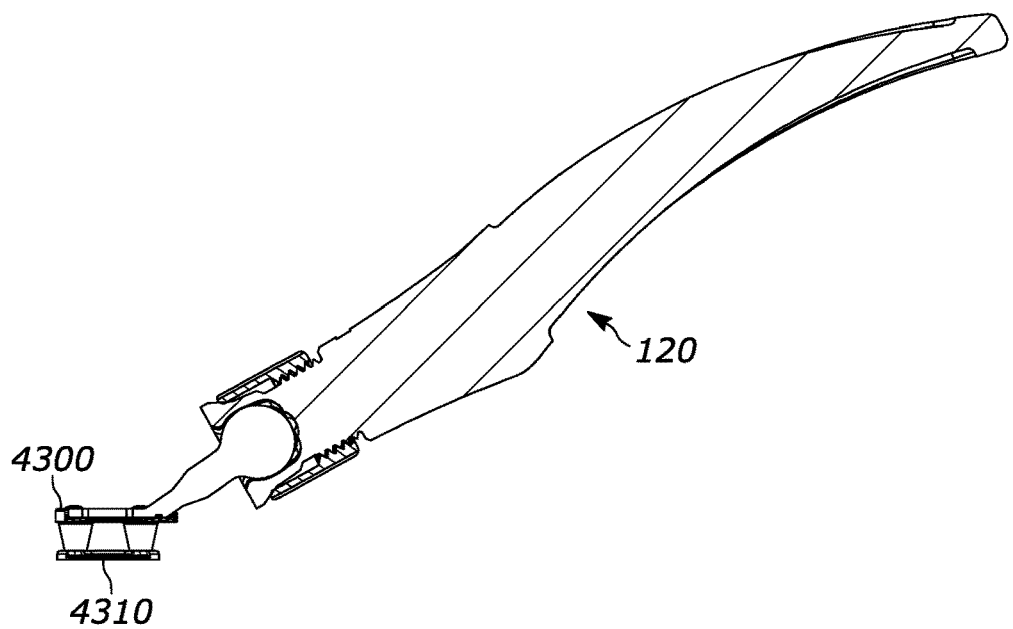
Figure 43E:
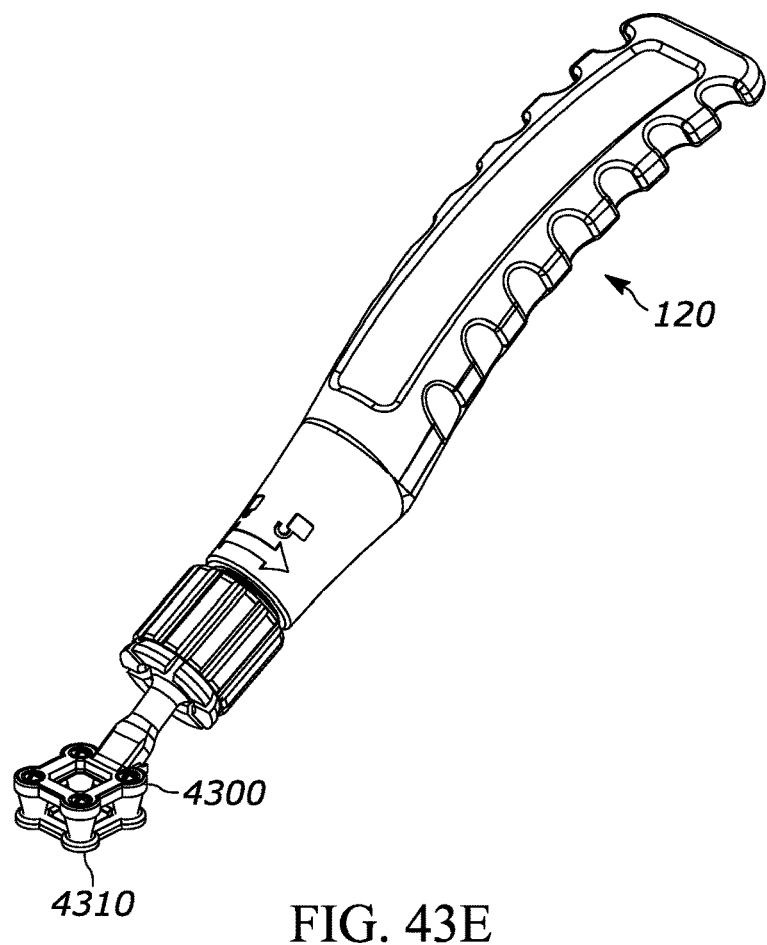

FIGS. 41A-41E show respective front, top, right side, cross section right, and isometric views of another embodiment consistent with present principles. It may be appreciated that many of the elements of this embodiment are the same as others described above (e.g., the handle 120), with the difference here being that a caddy/cartridge assembly 4100 and plate 4110 are configured in a dog bone shape as shown. FIG. 42A then shows an exploded isometric view of screws 4200 prior to being inserted into the assembly 4100. FIG. 42B shows an exploded side view, and 42C another exploded isometric view, of the same setup.

Figure 44A:
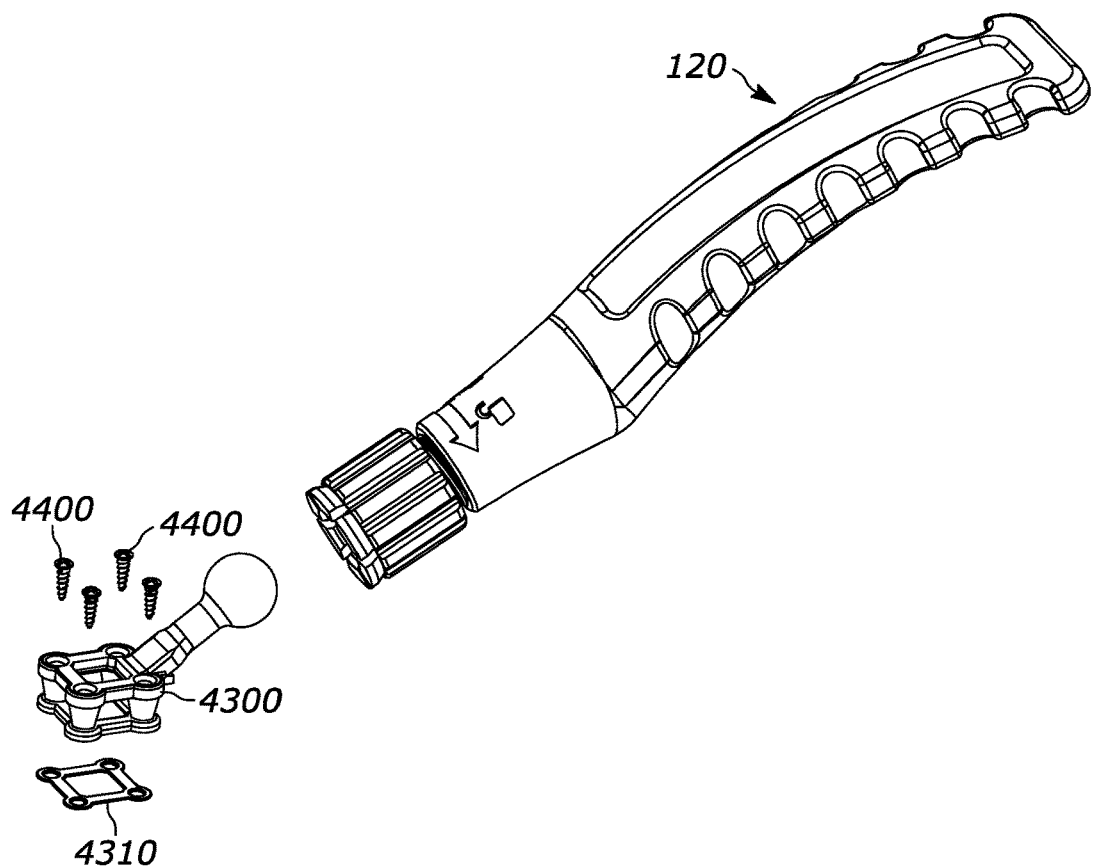
FIGS. 44A, 44B, and 44C show respective exploded isometric, exploded side, and exploded isometric views of the same setup as FIGS. 43A-43E.
Figure 44B:
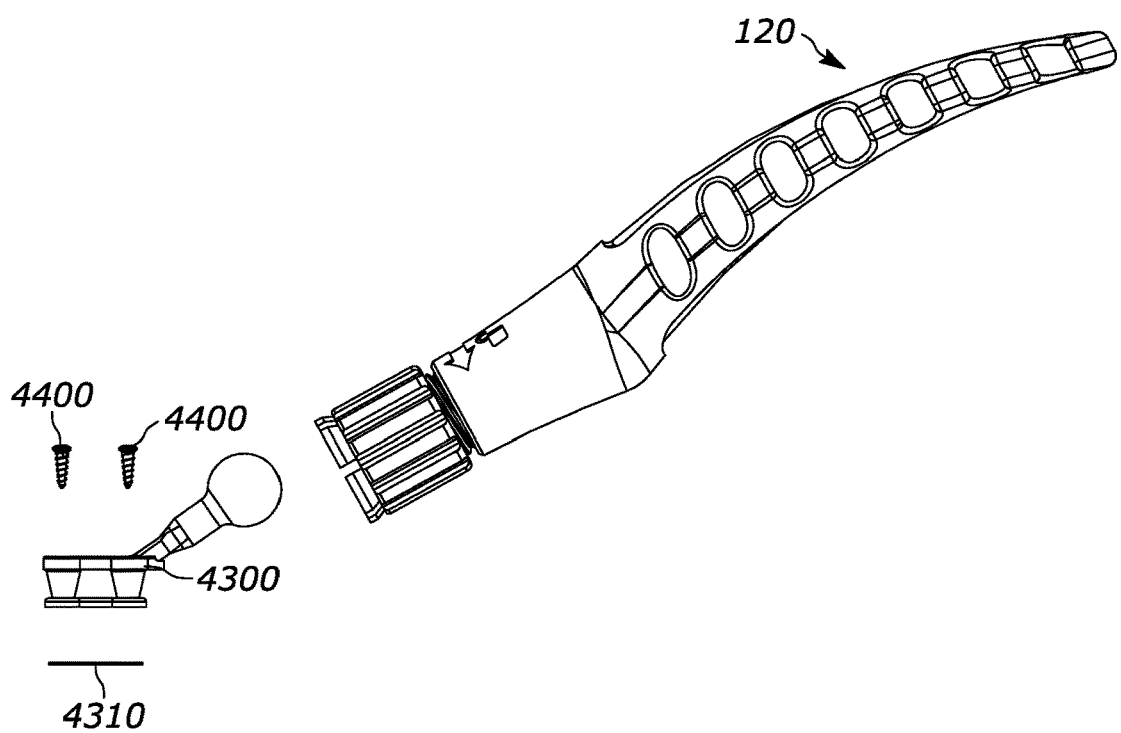
Figure 44C:
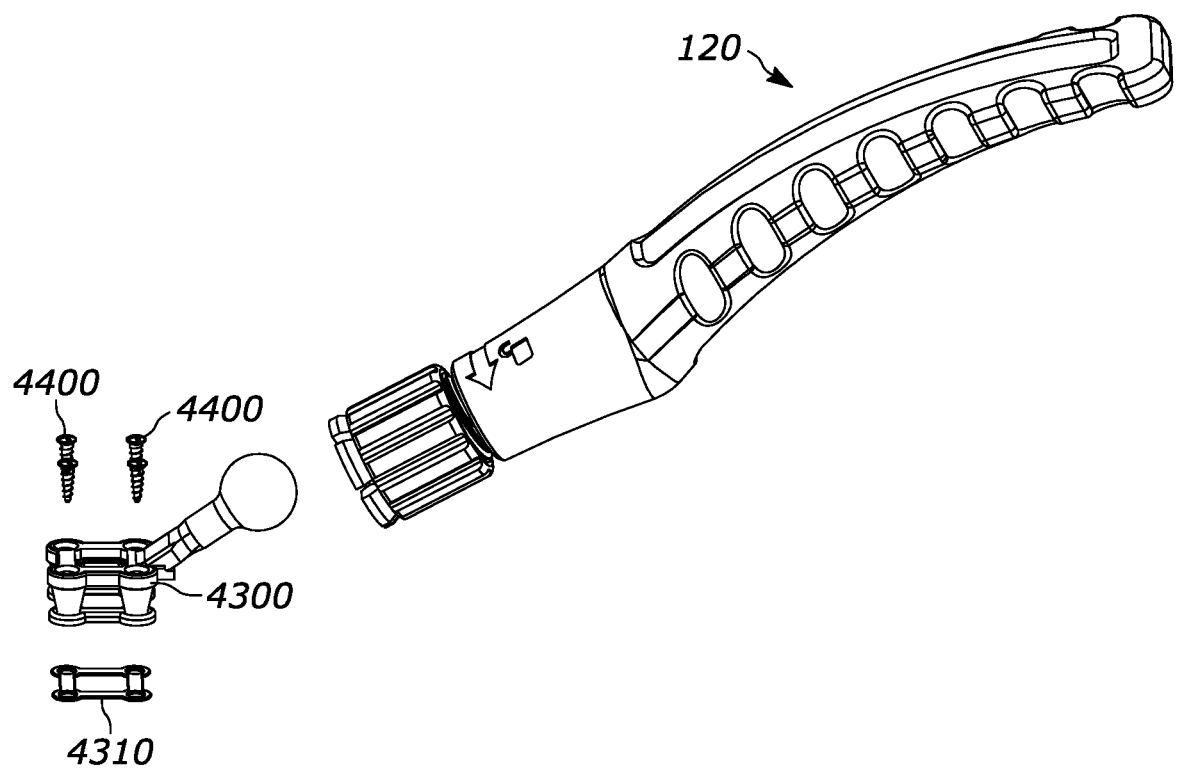

FIGS. 43A-43E show respective front, top, right side, cross section right, and isometric views of another embodiment consistent with present principles. It may be appreciated that many of the elements of this embodiment are the same as others described above (e.g., the handle 120), with the difference here being that a caddy/cartridge assembly 4300 and plate 4310 are configured in a square shape as shown. FIG. 44A then shows an exploded isometric view of screws 4400 prior to being inserted into the assembly 4300. FIG. 44B shows an exploded side view, and 44C another exploded isometric view, of the same setup. Note that per this setup, the bottom of the assembly 4300 may establish a boot-style plate holder similar to as described above in reference to FIG. 26, but in square shape.

It may now be appreciated that devices and methods have been disclosed related to surgical screw caddies/cartridge assemblies, where each opening/screw holder of the caddy may be reusable multiple times during a given surgery (e.g., multiple screws extended through the same opening on the caddy). The caddies may be sterile and relatively low-cost, including being sterilely packed for distribution.

In some specific examples, a kit may be manufactured, vended/provided, and/or used during a fracture reduction procedure consistent with present principles. The kit may include three or four (or even more) different cartridge assemblies/heads that can lock into an articulating handle. Screws and surgical plates to use with the rest of the kit may also be included in the kit. The surgeon may thus decide on the fly which plate/caddy combination to use depending on whatever circumstances the surgeon might encounter during the surgery.

Components included in one embodiment can be used in other embodiments in any appropriate combination. For example, any of the various components described herein and/or depicted in the Figures may be combined, interchanged, or excluded from other embodiments.

The term "a" or "an" in reference to an entity refers to one or more of that entity. As such, the terms "a" or "an", "one or more", and "at least one" can be used interchangeably herein.

"A system having at least one of A, B, and C" (likewise "a system having at least one of A, B, or C" and "a system having at least one of A, B, C") includes systems that have A alone, B alone, C alone, A and B together, A and C together, B and C together, and/or A, B, and C together, etc.

It is to be understood that whilst present principals have been described with reference to some example embodiments, these are not intended to be limiting, and that various alternative arrangements may be used to implement the subject matter claimed herein. Accordingly, while particular techniques and devices are herein shown and described in detail, it is to be understood that the subject matter which is encompassed by the present application is limited only by the claims.

What is claimed is:

1. A medical device, comprising:
    a cartridge comprising a first opening, the first opening configured to receive a screw, the first opening formed at least in part by a non-rigid elastomeric material, the non-rigid elastomeric material configured on the cartridge to stabilize the screw within the cartridge; and
    a rigid member that is unitary in being rigid and that is engaged with an upper surface of the cartridge, the rigid member comprising a second opening that aligns with the first opening for the screw to pass through the second opening and into the first opening for engagement with the non-rigid elastomeric material.

2. The medical device of claim 1, wherein the cartridge and rigid member establish at least part of a head that is engageable with a handle.

3. The medical device of claim 2, comprising the handle.

4. The medical device of claim 3, wherein the handle is integral with at least a portion of the head.

5. The medical device of claim 3, wherein the handle is detachable from the head.

6. The medical device of claim 5, comprising a ball and socket assembly, wherein the handle and head are engageable with each other via the ball and socket assembly, wherein the ball of the ball and socket assembly is disposed on the head, wherein the socket of the ball and socket assembly is disposed on the handle, and wherein the medical device comprises a locking mechanism to lock the ball into the socket to secure the head on the handle while still allowing articulation of the head with respect to the handle.

7. The medical device of claim 1, wherein the non-rigid elastomeric material comprises silicone.

8. The medical device of claim 1, wherein the non-rigid elastomeric material comprises thermoplastic elastomer.

9. The medical device of claim 1, comprising the screw.

10. The medical device of claim 1, wherein an exterior surface of the non-rigid elastomeric material tapers distally at a lower distal end portion to extend at least partially into a hole that aligns with the first and second openings, the hole being located in a surgical plate.

11. The medical device of claim 1, comprising an engagement mechanism extending downward from the rigid member to removably engage the cartridge with a surgical plate.

12. The medical device of claim 1, comprising a surgical plate through which the screw is extendable.

13. The medical device of claim 1, wherein the first and second openings are circular-bounded openings.

14. The medical device of claim 1, wherein the first and second openings are formed by the non-rigid elastomeric material of the cartridge.

15. The medical device of claim 1, wherein the cartridge and rigid member have respective structure for one or more of: snap-fit engagement of the cartridge with the rigid member, interference fit engagement of the cartridge with the rigid member.

16. The medical device of claim 1, wherein the non-rigid elastomeric material is over-molded onto the rigid member.

17. A device, comprising:
a cartridge comprising a first opening, the first opening configured to receive a surgical fastener, the first opening formed at least in part by a non-rigid material, the non-rigid material configured on the cartridge to stabilize the surgical fastener within the cartridge; and
an integrally-rigid rigid member engageable with an upper surface of the cartridge, the integrally-rigid rigid member comprising a second opening that aligns with the first opening for the surgical fastener to pass through the second opening and into the first opening for engagement with the non-rigid material.

18. The device of claim 17, comprising:
a surgical plate;
a mechanism for engaging the surgical plate with the cartridge.

19. The device of claim 17, wherein the first and second openings are circular-bounded openings.

20. A method, comprising:
providing a cartridge comprising a first opening, the first opening configured to receive a surgical fastener, the first opening formed at least in part by a non-rigid material, the non-rigid material configured on the cartridge to stabilize the surgical fastener within the cartridge; and
providing an integrally-rigid rigid member engageable with an upper surface of the cartridge, the integrally-rigid rigid member comprising a second opening that aligns with the first opening for the surgical fastener to pass through the second opening and into the first opening for engagement with the non-rigid material.

* * * * *